(12) United States Patent
Lurie et al.

(10) Patent No.: US 9,811,634 B2
(45) Date of Patent: Nov. 7, 2017

(54) SYSTEMS AND METHODS TO PREDICT THE CHANCES OF NEUROLOGICALLY INTACT SURVIVAL WHILE PERFORMING CPR

(71) Applicant: ResQSystems, Inc., Roseville, MN (US)

(72) Inventors: Keith Lurie, Minneapolis, MN (US); Anja Metzger, Stillwater, MN (US); Laura Puertas, Minneapolis, MN (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 339 days.

(21) Appl. No.: 14/262,423

(22) Filed: Apr. 25, 2014

(65) Prior Publication Data
US 2014/0324763 A1   Oct. 30, 2014

Related U.S. Application Data

(60) Provisional application No. 61/816,064, filed on Apr. 25, 2013.

(51) Int. Cl.
  *G06F 19/00* (2011.01)
(52) U.S. Cl.
  CPC ................ *G06F 19/3431* (2013.01)
(58) Field of Classification Search
  None
  See application file for complete search history.

(56) References Cited

U.S. PATENT DOCUMENTS

| | | | |
|---|---|---|---|
| 1,848,232 A | 3/1932 | Swope et al. |
| 2,325,049 A | 7/1943 | Frye et al. |
| 2,774,346 A | 12/1956 | Halliburton |
| 2,854,982 A | 10/1958 | Pagano |
| 2,904,898 A | 9/1959 | Marsden |
| 3,009,266 A | 11/1961 | Brook |

(Continued)

FOREIGN PATENT DOCUMENTS

| | | |
|---|---|---|
| AU | 1487792 B | 10/1992 |
| AU | 60539 B | 11/1994 |

(Continued)

OTHER PUBLICATIONS

N Azim, CY Wang. The use of bispectral index during a cardiopulmonary arrest: a potential predictor of cerebral perfusion. Anaesthesia 2004, vol. 59, p. 610-612.*

(Continued)

*Primary Examiner* — John S Brusca
*Assistant Examiner* — Olivia Wise
(74) *Attorney, Agent, or Firm* — The Webb Law Firm

(57) ABSTRACT

According to one aspect, a method for predicting the likelihood of survival of a particular individual with favorable neurological function during a cardiopulmonary resuscitation (CPR) procedure includes obtaining an electroencephalogram (EEG) signal of the particular individual during the CPR procedure. The method also includes obtaining a non-invasive measure of circulation of the particular individual during the CPR procedure and generating a prediction for the likelihood of survival of the particular individual with favorable neurological function based on the EEG signal and the non-invasive measure of circulation.

34 Claims, 7 Drawing Sheets

(56) References Cited

U.S. PATENT DOCUMENTS

| | | |
|---|---|---|
| 3,049,811 A | 8/1962 | Ruben |
| 3,068,590 A | 12/1962 | Padellford |
| 3,077,884 A | 2/1963 | Batrow et al. |
| 3,191,596 A | 6/1965 | Bird et al. |
| 3,199,225 A | 8/1965 | Robertson et al. |
| 3,209,469 A | 10/1965 | James |
| 3,216,413 A | 11/1965 | Arecheta Mota |
| 3,274,705 A | 9/1966 | Breakspear |
| 3,276,147 A | 10/1966 | Padellford |
| 3,307,541 A | 3/1967 | Hewson |
| 3,357,426 A | 12/1967 | Cohen |
| 3,420,232 A | 1/1969 | Bickford |
| 3,459,216 A | 8/1969 | Bloom et al. |
| 3,467,092 A | 9/1969 | Bird et al. |
| 3,509,899 A | 5/1970 | Hewson |
| 3,515,163 A | 6/1970 | Freeman |
| 3,523,529 A | 8/1970 | Kissen |
| 3,552,390 A | 1/1971 | Muller |
| 3,562,924 A | 2/1971 | Baerman et al. |
| 3,562,925 A | 2/1971 | Baermann et al. |
| 3,568,333 A | 3/1971 | Clark |
| 3,662,751 A | 5/1972 | Barkalow et al. |
| 3,669,108 A | 6/1972 | Sundblom et al. |
| 3,734,100 A | 5/1973 | Walker et al. |
| 3,739,776 A | 6/1973 | Bird et al. |
| 3,794,043 A | 2/1974 | McGinnis |
| 3,815,606 A | 6/1974 | Mazal |
| 3,834,383 A | 9/1974 | Weigl et al. |
| 3,872,609 A | 3/1975 | Smrcka |
| 3,874,093 A | 4/1975 | Garbe |
| 3,875,626 A | 4/1975 | Tysk et al. |
| 3,933,171 A | 1/1976 | Hay |
| 3,949,388 A | 4/1976 | Fuller |
| 3,973,564 A | 8/1976 | Carden |
| 3,981,398 A | 9/1976 | Boshoff |
| 3,993,059 A | 11/1976 | Sjostrand |
| 4,037,595 A | 7/1977 | Elam |
| 4,041,943 A | 8/1977 | Miller |
| 4,054,134 A | 10/1977 | Kritzer |
| 4,077,400 A | 3/1978 | Harrigan |
| 4,077,404 A | 3/1978 | Elam |
| 4,095,590 A | 6/1978 | Harrigan |
| 4,166,458 A | 9/1979 | Harrigan |
| 4,193,406 A | 3/1980 | Jinotti |
| 4,198,963 A | 4/1980 | Barkalow et al. |
| 4,226,233 A | 10/1980 | Kritzer |
| 4,237,872 A | 12/1980 | Harrigan |
| 4,240,419 A | 12/1980 | Furlong et al. |
| 4,259,951 A | 4/1981 | Chernack et al. |
| 4,262,667 A | 4/1981 | Grant |
| 4,297,999 A | 11/1981 | Kitrell |
| 4,298,023 A | 11/1981 | McGinnis |
| 4,316,458 A | 2/1982 | Hammerton-Fraser |
| 4,320,754 A | 3/1982 | Watson et al. |
| 4,326,507 A | 4/1982 | Barkalow |
| 4,331,426 A | 5/1982 | Sweeney |
| 4,349,015 A | 9/1982 | Alferness |
| 4,360,345 A | 11/1982 | Hon |
| 4,397,306 A | 8/1983 | Weisfeldt et al. |
| 4,424,806 A | 1/1984 | Newman et al. |
| 4,446,864 A | 5/1984 | Watson et al. |
| 4,448,192 A | 5/1984 | Stawitcke et al. |
| 4,449,526 A | 5/1984 | Elam |
| 4,481,938 A | 11/1984 | Lindley |
| 4,501,582 A | 2/1985 | Schulz |
| 4,513,737 A | 4/1985 | Mabuchi |
| 4,519,388 A | 5/1985 | Schwanbom et al. |
| 4,520,811 A | 6/1985 | White et al. |
| 4,533,137 A | 8/1985 | Sonne |
| 4,543,951 A | 10/1985 | Phuc |
| 4,588,383 A | 5/1986 | Parker et al. |
| 4,598,706 A | 7/1986 | Darowski et al. |
| 4,601,465 A | 7/1986 | Roy |
| 4,602,653 A | 7/1986 | Ruiz-Vela et al. |
| 4,637,386 A | 1/1987 | Baum |
| 4,738,249 A | 4/1988 | Linman et al. |
| 4,774,941 A | 10/1988 | Cook |
| 4,797,104 A | 1/1989 | Laerdal et al. |
| 4,807,638 A | 2/1989 | Sramek |
| 4,809,683 A | 3/1989 | Hanson |
| 4,827,935 A | 5/1989 | Geddes et al. |
| 4,828,501 A | 5/1989 | Ingenito et al. |
| 4,863,385 A | 9/1989 | Pierce |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,150,291 A | 9/1992 | Cummings et al. |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |
| 5,295,481 A | 3/1994 | Geeham |
| 5,301,667 A | 4/1994 | McGrail et al. |
| 5,305,743 A | 4/1994 | Brain |
| 5,306,293 A | 4/1994 | Zacouto |
| 5,312,259 A | 5/1994 | Flynn |
| 5,313,938 A | 5/1994 | Garfield et al. |
| 5,316,907 A | 5/1994 | Lurie et al. |
| 5,330,514 A | 7/1994 | Egelandsdal et al. |
| 5,335,654 A | 8/1994 | Rapoport |
| 5,353,788 A | 10/1994 | Miles |
| 5,355,879 A | 10/1994 | Brain |
| 5,359,998 A | 11/1994 | Lloyd |
| 5,366,231 A | 11/1994 | Hung |
| 5,377,671 A | 1/1995 | Biondi et al. |
| 5,383,786 A | 1/1995 | Kohnke |
| 5,388,575 A | 2/1995 | Taube |
| 5,392,774 A | 2/1995 | Sato |
| 5,395,399 A | 3/1995 | Rosenwald |
| 5,397,237 A | 3/1995 | Dhont et al. |
| 5,398,714 A | 3/1995 | Price |
| 5,413,110 A | 5/1995 | Cummings et al. |
| 5,423,685 A | 6/1995 | Adamson et al. |
| 5,423,772 A | 6/1995 | Lurie et al. |
| 5,425,742 A | 6/1995 | Joy |
| 5,437,272 A | 8/1995 | Fuhrman |
| 5,452,715 A | 9/1995 | Boussignac |
| 5,454,779 A | 10/1995 | Lurie et al. |
| 5,458,562 A | 10/1995 | Cooper |
| 5,468,151 A | 11/1995 | Egelandsdal et al. |
| 5,474,533 A | 12/1995 | Ward et al. |
| 5,477,860 A | 12/1995 | Essen-Moller |
| 5,490,820 A | 2/1996 | Schock et al. |
| 5,492,115 A | 2/1996 | Abramov et al. |
| 5,492,116 A | 2/1996 | Scarberry et al. |
| 5,496,257 A | 3/1996 | Kelly |
| 5,517,986 A | 5/1996 | Starr et al. |
| 5,544,648 A | 8/1996 | Fischer, Jr. |
| 5,549,106 A | 8/1996 | Gruenke et al. |

(56) References Cited

U.S. PATENT DOCUMENTS

| | | |
|---|---|---|
| 5,549,581 A | 8/1996 | Lurie et al. |
| 5,551,420 A | 9/1996 | Lurie et al. |
| 5,557,049 A | 9/1996 | Ratner |
| 5,580,255 A | 12/1996 | Flynn |
| 5,582,182 A | 12/1996 | Hillsman |
| 5,588,422 A | 12/1996 | Lurie et al. |
| 5,593,306 A | 1/1997 | Kohnke |
| 5,614,490 A | 3/1997 | Przybelski |
| 5,617,844 A | 4/1997 | King |
| 5,618,665 A | 4/1997 | Lurie et al. |
| 5,619,665 A | 4/1997 | Emma |
| 5,628,305 A | 5/1997 | Melker |
| 5,632,298 A | 5/1997 | Artinian |
| 5,643,231 A | 7/1997 | Lurie et al. |
| 5,645,522 A | 7/1997 | Lurie et al. |
| 5,657,751 A | 8/1997 | Karr, Jr. |
| 5,678,535 A | 10/1997 | DiMarco |
| 5,685,298 A | 11/1997 | Idris |
| 5,692,498 A | 12/1997 | Lurie et al. |
| 5,697,364 A | 12/1997 | Chua et al. |
| 5,701,883 A | 12/1997 | Hete et al. |
| 5,701,889 A | 12/1997 | Danon |
| 5,704,346 A | 1/1998 | Inoue |
| 5,720,282 A | 2/1998 | Wright |
| 5,722,963 A | 3/1998 | Lurie et al. |
| 5,730,122 A | 3/1998 | Lurie |
| 5,735,876 A | 4/1998 | Kroll et al. |
| 5,738,637 A | 4/1998 | Kelly et al. |
| 5,743,864 A | 4/1998 | Baldwin, II |
| 5,782,883 A | 7/1998 | Kroll et al. |
| 5,794,615 A | 8/1998 | Estes |
| 5,806,512 A | 9/1998 | Abramov et al. |
| 5,814,086 A | 9/1998 | Hirschberg et al. |
| 5,817,997 A | 10/1998 | Wernig |
| 5,823,185 A | 10/1998 | Chang |
| 5,823,787 A | 10/1998 | Gonzalez et al. |
| 5,827,893 A | 10/1998 | Lurie et al. |
| 5,832,920 A | 11/1998 | Field |
| 5,853,292 A | 12/1998 | Eggert et al. |
| 5,881,725 A | 3/1999 | Hoffman et al. |
| 5,885,084 A | 3/1999 | Pastrick et al. |
| 5,891,062 A | 4/1999 | Schock et al. |
| 5,896,857 A | 4/1999 | Hely et al. |
| 5,916,165 A | 6/1999 | Duchon et al. |
| 5,919,210 A | 7/1999 | Lurie et al. |
| 5,927,273 A | 7/1999 | Federowicz et al. |
| 5,937,853 A | 8/1999 | Strom |
| 5,941,710 A | 8/1999 | Lampotang et al. |
| 5,975,081 A | 11/1999 | Hood et al. |
| 5,977,091 A | 11/1999 | Nieman et al. |
| 5,984,909 A | 11/1999 | Lurie et al. |
| 5,988,166 A | 11/1999 | Hayek |
| 6,001,085 A | 12/1999 | Lurie et al. |
| 6,010,470 A | 1/2000 | Albery et al. |
| 6,029,667 A | 2/2000 | Lurie |
| 6,042,532 A | 3/2000 | Freed et al. |
| 6,062,219 A | 5/2000 | Lurie et al. |
| 6,078,834 A | 6/2000 | Lurie et al. |
| 6,086,582 A | 7/2000 | Altman et al. |
| 6,123,074 A | 9/2000 | Hete et al. |
| 6,131,571 A | 10/2000 | Lampotang et al. |
| 6,155,257 A | 12/2000 | Lurie et al. |
| 6,155,647 A | 12/2000 | Albecker, III |
| 6,165,105 A | 12/2000 | Boutellier et al. |
| 6,167,879 B1 | 1/2001 | Sievers et al. |
| 6,174,295 B1 | 1/2001 | Cantrell et al. |
| 6,176,237 B1 | 1/2001 | Wunderlich et al. |
| 6,193,519 B1 | 2/2001 | Eggert et al. |
| 6,209,540 B1 | 4/2001 | Sugiura et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie et al. |
| 6,296,490 B1 | 10/2001 | Bowden |
| 6,312,399 B1 | 11/2001 | Lurie et al. |
| 6,334,441 B1 | 1/2002 | Zowtiak et al. |
| 6,356,785 B1 | 3/2002 | Snyder et al. |
| 6,374,827 B1 | 4/2002 | Bowden et al. |
| 6,390,996 B1 | 5/2002 | Halperin et al. |
| 6,425,393 B1 | 7/2002 | Lurie et al. |
| 6,439,228 B1 | 8/2002 | Hete et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,970 B2 | 3/2003 | DeVries et al. |
| 6,526,973 B1 | 3/2003 | Lurie et al. |
| 6,536,432 B2 | 3/2003 | Truschel |
| 6,544,172 B2 | 4/2003 | Toeppen-Sprigg |
| 6,555,057 B1 | 4/2003 | Barbut et al. |
| 6,578,574 B1 | 6/2003 | Kohnke |
| 6,584,973 B1 | 7/2003 | Biondi et al. |
| 6,587,726 B2 | 7/2003 | Lurie et al. |
| 6,595,213 B2 | 7/2003 | Bennarsten |
| 6,604,523 B2 | 8/2003 | Lurie et al. |
| 6,622,274 B1 | 9/2003 | Lee et al. |
| 6,631,716 B1 | 10/2003 | Robinson et al. |
| 6,656,166 B2 | 12/2003 | Lurie et al. |
| 6,662,032 B1 | 12/2003 | Gavish et al. |
| 6,676,613 B2 | 1/2004 | Cantrell et al. |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie et al. |
| 7,066,173 B2 | 6/2006 | Banner et al. |
| 7,082,945 B2 | 8/2006 | Lurie |
| 7,096,866 B2 | 8/2006 | Be'eri et al. |
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 2001/0003984 A1 | 6/2001 | Bennarsten |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |

(56) References Cited

U.S. PATENT DOCUMENTS

| | | |
|---|---|---|
| 2002/0179090 A1 | 12/2002 | Boussignac |
| 2003/0000526 A1 | 1/2003 | Gobel |
| 2003/0037784 A1 | 2/2003 | Lurie |
| 2003/0062040 A1 | 4/2003 | Lurie et al. |
| 2003/0062041 A1 | 4/2003 | Keith et al. |
| 2003/0144699 A1* | 7/2003 | Freeman ............... A61B 5/00 607/5 |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0199566 A1 | 8/2007 | Be'eri |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0179442 A1 | 7/2010 | Lurie |
| 2010/0319691 A1 | 12/2010 | Lurie et al. |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |

FOREIGN PATENT DOCUMENTS

| | | |
|---|---|---|
| AU | 687942 B | 5/1995 |
| CA | 668771 A | 8/1963 |
| CA | 2077608 A1 | 3/1993 |
| CA | 2214887 C | 7/2008 |
| CN | 1183731 A | 6/1998 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0509773 A1 | 10/1992 |
| EP | 0560440 A1 | 9/1993 |
| EP | 0623033 A1 | 11/1994 |
| GB | 1344862 | 1/1974 |
| GB | 1465127 A | 2/1977 |
| GB | 2117250 A | 10/1983 |
| GB | 2139099 A | 11/1984 |
| JP | 2005000675 A | 1/2005 |
| JP | 2006524543 A | 11/2006 |
| JP | 2007504859 A | 3/2007 |
| WO | 9005518 A1 | 5/1990 |
| WO | 9302439 A1 | 2/1993 |
| WO | 9321982 A1 | 11/1993 |
| WO | 9426229 A1 | 11/1994 |
| WO | 9513108 A1 | 5/1995 |
| WO | 9528193 A1 | 10/1995 |
| WO | 9628215 A1 | 9/1996 |
| WO | 9820938 A1 | 5/1998 |
| WO | 9947197 A1 | 9/1999 |
| WO | 9963926 A2 | 12/1999 |
| WO | 0020061 A1 | 4/2000 |
| WO | 0102049 A2 | 1/2001 |
| WO | 0170092 A2 | 9/2001 |
| WO | 0170332 A2 | 9/2001 |
| WO | 2004096109 A3 | 11/2004 |
| WO | 2006088373 A1 | 8/2006 |
| WO | 2008147229 A1 | 12/2008 |
| WO | 2010044034 A1 | 4/2010 |
| WO | 2013064888 A1 | 5/2013 |
| WO | 2013096495 A1 | 6/2013 |
| WO | 2014026193 A1 | 2/2014 |

OTHER PUBLICATIONS

JY Jung, Y Kim, JE Klm. Usefulness of the bispectral index during cardiopulmonary resuscitation. Korean J Anesthesiol, Jan. 2013, vol. 64(1), p. 69-72.*

A Johnson, D Schweitzer, T Ahrens. Time to Throw Away Your Stethoscope? Capnography: Evidence-Based Patient Monitoring Technology. Journal of Radiology Nursing. 2011, vol. 30, Issue 1, p. 25-34.*

Advanced Circulatory Systems, Inc. (2006). ResQPOD® Circulatory Enhancer: Strengthening the Chain of Survival (#49-0336-000, 02). [Brochure]. Roseville,MN: Advanced Circulatory Systems,Inc., 2 pages.

Advanced Circulatory Systems, Inc. (2006). ResQPOD® Circulatory Enhancer: Strengthening the Chain of Survival (#49-0336-000, 01) [Brochure]. Roseville, MN: Advanced Circulatory Systems, Inc., 2 pages.

Advanced Circulatory Systems. Inc. (2011). ResQPOD® Perfusion on Demand: ResQPOD Impedance Threshold Device (#49-0324-001, 05) [Brochure]. Roseville, MN: Advanced Circulatory Systems, Inc., 2 pages.

Advanced Circulatory Systems, Inc. (2011). ResQPOD® Perfusion on Demand: ResQPOD Impedance Threshold Device (#49-0324-001, 04) [Brochure]. Roseville, MN: Advanced Circulatory Systems, Inc., 2 pages.

Advanced Circulatory Systems, Inc. (2010). ResQPOD® Perfusion on Demand: ResQPOD Impedance Threshold Device (#49-0324-001, 03) [Brochure]. Roseville, MN: Advanced Circulatory Systems, Inc., 2 pages.

Advanced Circulatory Systems, Inc. (2009). ResQPOD® Perfusion on Demand: ResQPOD Impedance Threshold Device (#49-0324-001, 02) [Brochure]. Roseville, MN: Advanced Circulatory Systems, Inc., 2 pages.

Advanced Circulatory Systems, Inc. (2005). Introducing ResQPOD® (#49-0324-000, 01) [Brochure]. Roseville, MN: Advanced Circulatory Systems. Inc., 2 pages.

(56) References Cited

OTHER PUBLICATIONS

Ambu International A/S "Directions for use of Ambu® CardioPump™", Sep. 1992, 8 pages.
Aufderheide, T., et al., "Standard cardiopulmonary resuscitation versus active compression-decompression cardiopulmonary resuscitation with augmentation of negative intrathoracic pressure for out-of-hospital cardiac arrest: A randomized trial" 2011, Lancet, vol. 377, pp. 301-311.
Babbs, Charles F.MD. PhD., "CPR Techniques that Combine Chest and Abdominal Compression and Decompression: Hemodynamic Insights from a Spreadsheet Model", Circulation,1999, pp. 2146-2152.
Christenson, J.M. "Abdominal Compressions During CPR: Hemodynamic Effects of Altering Timing and Force", The Journal of Emergency Medicine, vol. 10, pp. 257-266, 1992.
Cohen, Todd J. et a.l . "Active Compression-Decompression Resuscitation: a Novel Method of Cardiopulmonary Resuscitation", Department of Medicine and the Cardiovascular Research Institute, UC San Francisco, American Heart Journal 124(5):1145-1150, 1992.
Cohen, Todd J. et al., "Active Compression-Decompression: A New Method of Cardiopulmonary Resuscitation", JAMA 267(21): 2916-2923 (Jun. 3, 1992).
Dupuis, Yvon G., Ventilators—Theory and ClinicalApplication, pp. 447-449, 481, 496; Jan. 1986, Mosby Company.
Geddes, L.A. et al., "Inspiration Produced by Bilateral Electromagnetic, Cervical Phrenic Nerve Stimulation in Man," IEEE Transactions on Biomedical Engineering 38(9): 1047-1048 (Oct. 1991).
Geddes, L.A. et al., "Optimum Stimulus Frequency for Contracting the Inspiratory Muscles with Chest Surface Electrodes to Produce Artificial Respiration," Annals of Biomedical Engineering 18:103-108 (1990).
Geddes, L.A., "Electrically Produced Artificial Ventilation," Medical Instrumentation 22(5): 263-271 (1988).
Geddes, L.A., "Electroventilation—A Missed Opportunity?", Biomedical Instrumentation & Technology, Jul./Aug. 1998, pp. 401-414.
Glenn, William W.L. et al.,"Diaphragm Pacing by Electrical Stimulation of the Phrenic Nerve," Neurosurgery 17(6): 974-984 (1985).
Glenn, William W.L., et al., "Twenty Years of Experei nce in Phrenic Nerve Stimulation to Pace the Diaphragm," Pace 9: 780-784 (Nov./Dec. 1986, Part I).
Kotze, P.L. et al., "Diaphragm Pacing in the Treatment of Ventilatory Failure," San. Deel 68:223-224 (Aug. 17, 1995).
Laghi, Franco et al., "Comparison of Magnetic and Electrical Phrenic Nerve Stimulation in Assessment of Diaphragmantic Contractility," American Physiological society, pp. 1731-1742 (1996).
Linder, Karl H. et al., "Effects of Active Compression-Decompression Resuscitation on Myocardial and Cerebral Blood Flow in Pigs." Department of Anesthesiology and CriticalCare Medicine, University of Ulm, Germany, Circulation 88(3):1254-1263,(Oct. 7, 1993).
Aufderheide,T.,et al.,"Hyperventilation-induced hypotension during cardiopulmonary resuscitation," Circulation ; Apr. 27, 2004; 109(16):1960-1965.
Lurie, Keith G. et al., "Regulated to Death: The Matter of Informed Consent for Human Experimentation in Emergency Resuscitation Research," Cardiac Arrhythmia Center at the University of Minnesota, PACE 18:1443-1447 (Jul. 1995).
Michigan Instruments, Inc.,"Thumper 1007CC Continuous Compression Cardiopulmonary Resuscitation System", obtained online 715/2006 at http://www.michiganinstruments.com/resus-thumper. htm, 2 pages.
Mushin, W. W. et al., "Automatic Ventilation of the Lungs—The Lewis-Leigh Inflating Valve," Blackwell Scientific, Oxford, GB, p. 838.
Schultz, J., et al., "Sodium nitroprusside enhanced cardiopulmonary resuscitation (SNPeCPR) Improves Vitalorgan Perfusion Pressures and Carotid Blood Flow in a Porcine Model of Cardiac Arrest," Resuscitation, 2012, vol. 83, pp. 374-377.

Segal, N., et al., "Ischemic Postconditioning at the Initiation of Cardiopulmonary Resuscitation Facilitates Cardiac and Cerebral Recovery After Prolonged Untreated Ventricular Fibrillation," Resuscitation , Apr. 18, 2012, 7 pages.
Yannopoulos, D., et al., "Controlled Pauses at the Initiation of Sodium Nitroprussidee-enhanced Cardiopulmonary Resuscitation Facilitate Neurological and Cardiac Recovery after 15 Minutes of Untreated Ventricular Fibrillation," Critical Care Medicine , 2012, vol. 40, No. 5, 8 pages.
Yannopoulos, Demetris et al., "Intrathoracic Pressure Regulator During Continuous-Chest-Compression Advanced Cardiac Resuscitation Improves Vital Organ Perfusion Pressures in a Porcine Model of Cardiac Arrest", Circulation, 2005, pp. 803-811.
Yannopoulos, D., et al., "Intrathoracic Pressure Regulation Improves 24 Hour Survival in a Porcine Model of Hypovolemic Shock." Anesthesia & Angalgesia . ITPR and Survival in Hypovolemic Shock, vol. 104, No. 1, Jan. 2007, pp. 157-162.
Yannopoulos, D.,et al., "Intrathoracic Pressure Regulation Improves Vital Organ Perfusion Pressures in Normovolemic and Hypovolemic Pigs," Resuscitation, 2006, 70, pp. 445-453.
Yannopoulos, D., et al., "Sodium Nitroprusside Enhanced Cardiopulmonary Resuscitation Improves Survival with Good Neurological Function in a Porcine Model of Prolonged Cardiac Arrest," Critical Care Medicine. 2011, vol. 39, No. 6, 6 pages.
Zoll Autopulse Non-Invasive Cardiac Support Pump, obtained online on 715106 at http://www.zoll.com/product.aspx?id=84, 1 page.
Advanced Circulatory Systems, Inc. (Jan. 2014), Emerging Data: The Resuscitation Outcomes Consortium (ROC) Primed Study on the Efficacy of the ITD (#49-0864-000,06) [Brochure], Roseville, MN:Advanced Circulatory Systems, Inc. 2 pages.
Advanced Circulatory Systems, Inc. (Jan. 2013), Emerging Data: The Resuscitation Outcomes Consortium (ROC) Primed Study on the Efficacy of the ITD (#49-0864-000,05) [Brochure], Roseville, MN:Advanced Circulatory Systems, Inc. 2 pages.
Advanced Circulatory Systems, Inc. (Mar. 2012), Benefits of the ResQPOD Based Upon the ROC PRIMED Study (#49-0864-000,04) [Brochure], Roseville, MN:Advanced Circulatory Systems, Inc. 2 pages.
Advanced Circulatory Systems, Inc. (Jan. 2012), Benefits of the ResQPOD Based Upon the ROC PRIMED Study (#49-0864-000,03) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,01) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,02) [Brochure], Roseville, MN:Advanced Circulatory Systems, Inc. 2 pages.
Advanced Circulatory Systems, Inc. (2013), ResQPOD More than a Heartbeat (#49-0336-000,08) [Brochure], Roseville, MN:Advanced Circulatory Systems, Inc. 2 pages.
Advanced Circulatory Systems, Inc. (2011), ResQPOD ITD:Strengthening the Chain of Survival (#49-0336000,06) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,05) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,04) [Brochure], Roseville, MN:Advanced Circulatory Systems, Inc. 2 pages.
Advanced Circulatory Systems, Inc. (2010), ResQPOD Impedance Threshold Device 10.0:Strengthening the Chain of Survival (#49-0336000,03) [Brochure], Roseville, MN:Advanced Circulatory Systems, Inc. 2 pages.
Advanced Circulatory Systems, Inc. (2006). ResQPOD® Circulatory Enhancer: Strengthening the Chain of Survival (#49-0336-000, 02). [Brochure]. Roseville.MN: Advanced Circulatory Systems, Inc., 2 pages.

(56) References Cited

OTHER PUBLICATIONS

Advanced Circulatory Systems, Inc. (2006). ResQPOD® Circulatory Enhancer: Strengthening the Chain of Survival (#49-0336-000, 01) [Brochure]. Roseville, MN: Advanced Circulatory Systems, Inc.. 2 pages.

Advanced Circulatory Systems. Inc. (2011). ResQPOD® Perfusion on Demand: ResQPOD Impedance Threshold Device (#49-0324-001, 05) [Brochure]. Roseville, MN: Advanced Circulatory Systems, Inc., 2 pages.

Advanced Circulatory Systems, Inc. (2011). ResQPOD® Perfusion on Demand: ResQPOD Impedance Threshold Device (#49-0324-001, 04) [Brochure]. Roseville, MN: Advanced Circulatory Systems, Inc.. 2 pages.

Advanced Circulatory Systems,Inc. (2010). ResQPOD® Perfusion on Demand: ResQPOD Impedance Threshold Device (#49-0324-001, 03) [Brochure]. Roseville, MN: Advanced Circulatory Systems, Inc., 2 pages.

Advanced Circulatory Systems,Inc. (2009). ResQPOD® Perfusion on Demand: ResQPOD Impedance Threshold Device (#49-0324-001, 02) [Brochure]. Roseville, MN: Advanced Circulatory Systems, Inc., 2 pages.

Advanced Circulatory Systems,Inc. (2005). Introducing ResQPOD® (#49-0324-000, 01) [Brochure]. Roseville, MN: Advanced Circulatory Systems, Inc., 2 pages.

Ambu InternationalNS Directions for use of Ambu® CardioPump™•. Sep. 1992, 8 pages.

Aufderheide, T., et al., "Standard cardiopulmonary resuscitation versus active compression-decompression cardiopulmonary resuscitation with augmentation of negative intrathoracic pressure for out-of-hospital cardiac arrest: A randomized tria,l" 2011, Lancet, vol. 377, pp. 301-311.

Babbs, Charles F.MD. PhD., CPR Techniques that Combine Chest and AbdominalCompression and Decompression: Hemodynamic Insights from a Spreadsheet Model, Circulation,1999, pp. 2146-2152.

Christenson, J.M.. "Abdominal Compressions During CPR: Hemodynamic Effects of Altering Timing and Force", The Journal of Emergency Medicine, vol. 10, pp. 257-266, 1992.

Dupuis, Yvon G., Ventilators—Theory and Clinical Application, pp. 447-448, 481, 496; Jan. 1986, Mosby Company.

Geddes, L.A. et al., "Electrically Produced Artificial Ventilation," Medical Instrumentation, vol. 22(5); 263-271, 1988.

Glenn, William W.L, et al., "Twenty Years of Experience in Phrenic Nerve Stimulation to Pace the Diaphragm," Pace 9: 780-784 (Nov./Dec. 1986, Part I).

Guidelines for Cardiopulmonary Resuscitation and Emergency Cardiac Care, JAMA, 1992:268;2172-2177.

Kotze, P.L. et al., "Diaphragm Pacing in the Treatment of Ventilatory Failure,"San. Deel68:223-224 (Aug. 17, 1995).

Lindner, Karl H. et al., "Effects of Active Compression-Decompression Resuscitation on Myocardialand Cerebral Blood Flow in Pigs," Department of Anesthesiology and CriticalCare Medicine, University of Ulm, Germany, Circulation 88 (3):1254-1263,(Oct. 7, 1993).

Aufderheide,T.,et al.,"Hyperventilation-induced hypotension during cardiopulmonary resuscitation," Circulation ; Apr. 27, 2004; 109(16):1960-5.

Lurie, K., et. Al., Comparison of a 10-Breaths-Per-Minute Versus a 2-Breaths-Per-Minute Strategy During Cardiopulmonary Resuscitation in a Porcine Model of Cardiac Arrest,: Respiratory Care, 2008, vol. 53, No. 7, pp. 862-870.

Michigan Instruments, Inc.Thumper 1007CC Continuous Compression Cardiopulmonary Resuscitation System, obtained online Jul. 15, 2006 at http://WwW.michiganinstruments.com/resus-thumper.htm, 2 pages.

Mushin W. W. et al., "Automatic Ventilation of the Lungs—The Lewis-Leigh Inflating Valve," Blackwell Scientific, Oxford, GB, p. 838.

Schultz, J., et al., "Sodium nitroprusside enhanced cardiopulmonary resuscitation (SNPeCPR) improves vitalorgan perfusion pressures and carotid blood flow in a porcine modelof cardiac arrest," Resuscitation, 2012, vol. 83, pp. 374-377.

Shapiro et al., "Neurosurgical Anesthesia and Intracranial Hypertension" Chapter 54, Anesthesia; 3rd Edition; Ed. Ron Miller 1990.

Yannopoulos, D., et al., "Controlled pauses at the initiation of sodium nitroprussdi e-enhanced cardiopulmonary resuscitation facilitate neurological and cardiac recovery after 15 minutes of untreated ventricular fibrillation," Critical Care Medicine , 2012, vol. 40, No. 5, 8 pages.

Yannopoulos, Demetris et al., "Intrathoracic Pressure Regulator During Continuous-Chest-Compression Advanced Cardiac Resuscitation Improves Vital Organ Perfusion Pressures in a Porcine Modelof Cardiac Arrest", Circulation, 2005, pp. 803-811.

Yannopoulos, D., et al.,"Intrathoracic Pressure Regulation Improves 24-Hour Survival in a Porcine Model of Hypovolemic Shock." Anesthesia & Analgesia . ITPR and Survival in Hypovolemic Shock, vol. 104, No. 1, Jan. 2007, pp. 157-162.

Yannopoulos. D.,et al.,"Intrathoracic pressure regulation improves vital organ perfusion pressures in normovolemic and hypovolemic pigs," Resuscitation, 2006, 70, pp. 445-453.

Yannopoulos, D., et al.,"Sodium nitroprusside enhanced cardiopulmonary resuscitation improves survival with good neurological function in a porcine model of prolonged cardiac arrest," Critical Care Medicine. 2011, vol. 39, No. 6, 6 pages.

Zhao, et. Al., Inhibation of a Myocardial Injury by Ischemic Postconditioning During RePerfusion:Comparison with Ischemic Preconditioning, Am. J. Physiol Heart Circ 285: H579-H588 (2003).

Zoll Autopulse Non-Invasive Cardiac Support Pump, obtained online on 715106 at http://www.zoll.com/product.aspx?id=84,1 page.

Kroll et al., Withdrawn U.S. Pat. No. 5,584,866, published Dec. 17, 1996.

* cited by examiner

Fig. 1 BIS and ETCO2 after 6 minutes VF during differing types of CPR, n=3 and a photo of the BIS screen during a typical study.

SYSTEMS AND METHODS TO PREDICT THE CHANCES OF NEUROLOGICALLY INTACT SURVIVAL WHILE PERFORMING CPR

CROSS-REFERENCE TO RELATED APPLICATIONS

This application claims priority to U.S. Provisional Patent Application No. 61/816,064 filed 25 Apr. 2013, entitled "SYSTEMS AND METHODS TO PREDICT THE CHANCES OF NEUROLOGICALLY INTACT SURVIVAL WHILE PERFORMING CPR," the entire disclosure of which is hereby incorporated by reference, for all purposes, as if fully set forth herein.

BACKGROUND

Cardiac arrest is one of the leading causes of death in the United States. As a result, a number of approaches to treating cardiac arrest have been developed, which have resulted in significant clinical advances in the field. Despite this progress, greater than 80% of patients who experience sudden and unexpected out of hospital cardiac arrest (OHCA) cannot be successfully resuscitated. The prognosis is particularly grim in patients with a prolonged time between cardiac arrest and the start of cardiopulmonary resuscitation (CPR).

Recent advances in techniques to optimize blood flow to the heart and brain during CPR reduce reperfusion injury and improve post-resuscitation restoration of brain function. The recent advances may include therapeutic hypothermia and/or other procedures, which may significantly improve the likelihood for survival with favorable neurological function. At present, however, rescuer personnel typically terminate their resuscitation efforts based upon the duration of CPR performed without a guide as to whether or not the patient actually has a chance to survive and thrive. Consequently, it may be difficult to identify during administration of CPR those patients that may and may not be able to be resuscitated and wake up after successful resuscitation.

SUMMARY

The present disclosure is directed to systems and methods for predicting the likelihood of neurologically intact survival while performing cardiopulmonary resuscitation. In particular, and as discussed throughout, spectral analysis of electroencephalogram signals measured during cardiopulmonary resuscitation may be used as a predictor, exclusively or in combination with a non-invasive measure of perfusion or circulation, to determine the chances of a favorable outcome of performing cardiopulmonary resuscitation.

In an aspect, a method for predicting the likelihood of survival of a particular individual with favorable neurological function during a cardiopulmonary resuscitation (CPR) procedure is disclosed. The method may include obtaining an electroencephalogram (EEG) signal of the particular individual during the CPR procedure. The method may include obtaining a non-invasive measure of circulation of the particular individual during the CPR procedure. The method may include generating a prediction for the likelihood of survival of the particular individual with favorable neurological function based on the EEG signal and the non-invasive measure of circulation.

Additionally, or alternatively, the method may include performing an intrathoracic pressure regulation procedure or a reperfusion injury protection procedure during the CPR procedure. It is contemplated that any of a number of such procedures may be performed during the CPR procedure such as, for example, performing a stutter CPR procedure, administering anesthetics at or during the CPR procedure, administering sodium nitroprusside in connection with the CPR procedure, etc. Examples of such procedures and techniques are described in, for example, U.S. patent application Ser. Nos. 12/819,959, 13/026,459, 13/175,670, 13/554,986, 61/509,994, and 61/577,565, each of which are incorporated herein by reference.

Additionally, or alternatively, the method may include generating the prediction for the likelihood of survival of the particular individual with favorable neurological function on a mathematical product of the EEG signal and the non-invasive measure of circulation. It is contemplated however that one or more other mathematical operations may be performed to generate an indicator or predictor for the likelihood of survival of a particular individual with favorable neurological function.

Additionally, or alternatively, the method may include measuring the EEG signal using a bispectral index monitor. It is contemplated however that any device or system configured to measure an EEG signal may be used to measure or otherwise sense the same.

Additionally, or alternatively, the method may include obtaining the non-invasive measure of circulation of the particular individual by monitoring the concentration or partial pressure of carbon dioxide in respiratory gases of the particular individual. It is contemplated however that other means such as diffuse correlation spectroscopy or impedance changes measured across the thorax or other body parts could also be used as a non-invasive measure of circulation during CPR.

Additionally, or alternatively, the method may include determining whether sedation is needed during or following the CPR procedure based on the EEG signal and the non-invasive measure of circulation. Here, when the EEG signal or a product, for example, of the EEG signal and a measure of circulation (e.g., end tidal CO2) reaches a threshold value during CPR, then a care provider may know that it may be appropriate to deliver a low dose of a sedative, such as medazelam for example, to prevent the patient undergoing cardiac arrest or from becoming too agitated.

Additionally, or alternatively, the method may include extracting respiratory gases from the airway of the particular individual to create an intrathoracic vacuum that lowers pressure in the thorax in order to achieve at least one of: enhancing the flow of blood to the heart of the particular individual; lowering intracranial pressures of the particular individual; and enhancing cerebral profusion pressures of the particular individual. It is contemplated, however, that any device or system that is configured to create a vacuum and that may be coupled to an individual so as to create an intrathoracic vacuum may be used to lower pressure in the thorax and/or to artificially inspire, such as a ventilator, iron lung cuirass device, a phrenic nerve stimulator, and many others.

Additionally, or alternatively, the method may include at least periodically delivering a positive pressure breath to the particular individual to provide ventilation. Such an implementation may be consistent with a CPR procedure.

Additionally, or alternatively, the method may include preventing air from at least temporarily entering the particular individual's lungs during at least a portion of a relaxation or decompression phase of the CPR procedure to create an intrathoracic vacuum that lowers pressure in the thorax in order to achieve at least one of: enhanced flow of blood to the heart of the particular individual; lowered intracranial pressures of the particular individual; and enhanced cerebral profusion pressures of the particular individual. It is contemplated that any device or system that is configured to prevent air from at least temporarily entering the particular individual's lungs may be used to implement the same. For example, a valve system may be used to prevent air from at least temporarily entering the particular individual's lungs. Other embodiments are possible.

In an aspect, a computing system configured for predicting the likelihood of survival of a particular individual with favorable neurological function during a cardiopulmonary resuscitation (CPR) procedure is described. The computing device includes a module that is configured to obtain an electroencephalogram (EEG) signal of the particular individual during the CPR procedure and a module that is configured to obtain a non-invasive measure of circulation of the particular individual during the CPR procedure. The computing system also includes a module that is configured to output a prediction for the likelihood of survival of the particular individual with favorable neurological function based on EEG signal and the non-invasive measure of circulation.

In some embodiments, the computing system further includes a bispectral index monitor that is configured to calculate a bispectral index value of the particular individual based on the EEG signal. In some embodiments, the module that is configured to obtain the non-invasive measure of circulation is a capnography monitor that is configured to calculate the non-invasive measure of circulation of the particular individual. In some embodiments, the module that is configured to output the prediction for the likelihood of survival is a computing device processor. In such embodiments, the prediction of the likelihood of survival may be based on a bispectral index value and the non-invasive measure of circulation.

In some embodiments, the module that is configured to obtain the EEG signal is an EEG sensor. In some embodiments, the non-invasive measure of circulation of the particular individual is a measure of concentration or partial pressure of carbon dioxide in respiratory gases of the particular individual. In some embodiments, the computing system further includes a module that is configured to determine whether sedation is needed during and/or following the CPR procedure based on the non-invasive measure of circulation and a bispectral index value calculated from the EEG signal. In such embodiments, the module may be a computing device processor.

In an aspect, an apparatus configured and arranged for predicting the likelihood of survival of a particular individual with favorable neurological function during a cardiopulmonary resuscitation (CPR) procedure is disclosed. The apparatus may include a circulation enhancement device that is configured to enhance a person's circulation while performing CPR on the person. The apparatus may include an EEG sensor that is configured to measure an EEG signal of the person. The apparatus may include a non-invasive sensor to measure circulation data on the person's circulation.

Additionally, or alternatively, the apparatus may include a bispectral index monitor for measuring the EEG signal, and a capnography monitor to measure circulation data on the person's circulation.

Additionally, or alternatively, the apparatus may include a computing device having a processor that is configured to receive and process the EEG signal and the circulation data, and to produce a prediction of the likelihood of survival of the person with favorable neurological function.

Additionally, or alternatively, the circulation enhancement device may be selected from the group consisting of: a vacuum source; and a pressure responsive valve.

Additionally, or alternatively, the apparatus may include a vacuum source configured to extract respiratory gases from the airway of the person to create an intrathoracic vacuum to lower pressures in the thorax, wherein the vacuum source comprises an impeller that creates the vacuum, and wherein the pressures are lowered in the thorax in order to achieve at least one of: enhanced flow of blood to the heart of the particular individual; lower pressures in the thorax in order to lower intracranial pressures of the person; and lower pressures in the thorax in order to enhance cerebral profusion pressures of the person.

Additionally, or alternatively, the apparatus may include a pressure responsive valve configured to prevent respiratory gases from entering the lungs during at least a portion of a relaxation or decompression phase of CPR to create an intrathoracic vacuum that lowers pressure in the thorax in order to achieve at least one of: enhanced flow of blood to the heart of the particular individual; lowered intracranial pressures of the particular individual; and enhanced cerebral profusion pressures of the particular individual.

In an aspect, a method for determining whether sedation is needed while performing cardiopulmonary resuscitation (CPR) on a particular individual is disclosed. The method may include obtaining an electroencephalogram (EEG) signal of the particular individual during a CPR procedure. The method may include obtaining a non-invasive measure of circulation of the particular individual during the CPR procedure. The method may include determining whether to sedate the individual while performing CPR based upon the product of the EEG signal and a non-invasive measure of circulation.

In an aspect, a method for determining whether sedation is needed after concluding cardiopulmonary resuscitation (CPR) on a particular individual is disclosed. The method may include obtaining an electroencephalogram (EEG) signal of the particular individual during a CPR procedure. The method may include obtaining a non-invasive measure of circulation of the particular individual during the CPR procedure. The method may include determining whether to sedate the individual after performing CPR based upon the product of the EEG signal and a non-invasive measure of circulation.

Although not so limited, an appreciation of the various aspects of the present disclosure may be obtained from the following description in connection with the drawings.

BRIEF DESCRIPTION OF THE DRAWINGS

The present invention is described in conjunction with the appended figures.

Figure 1:
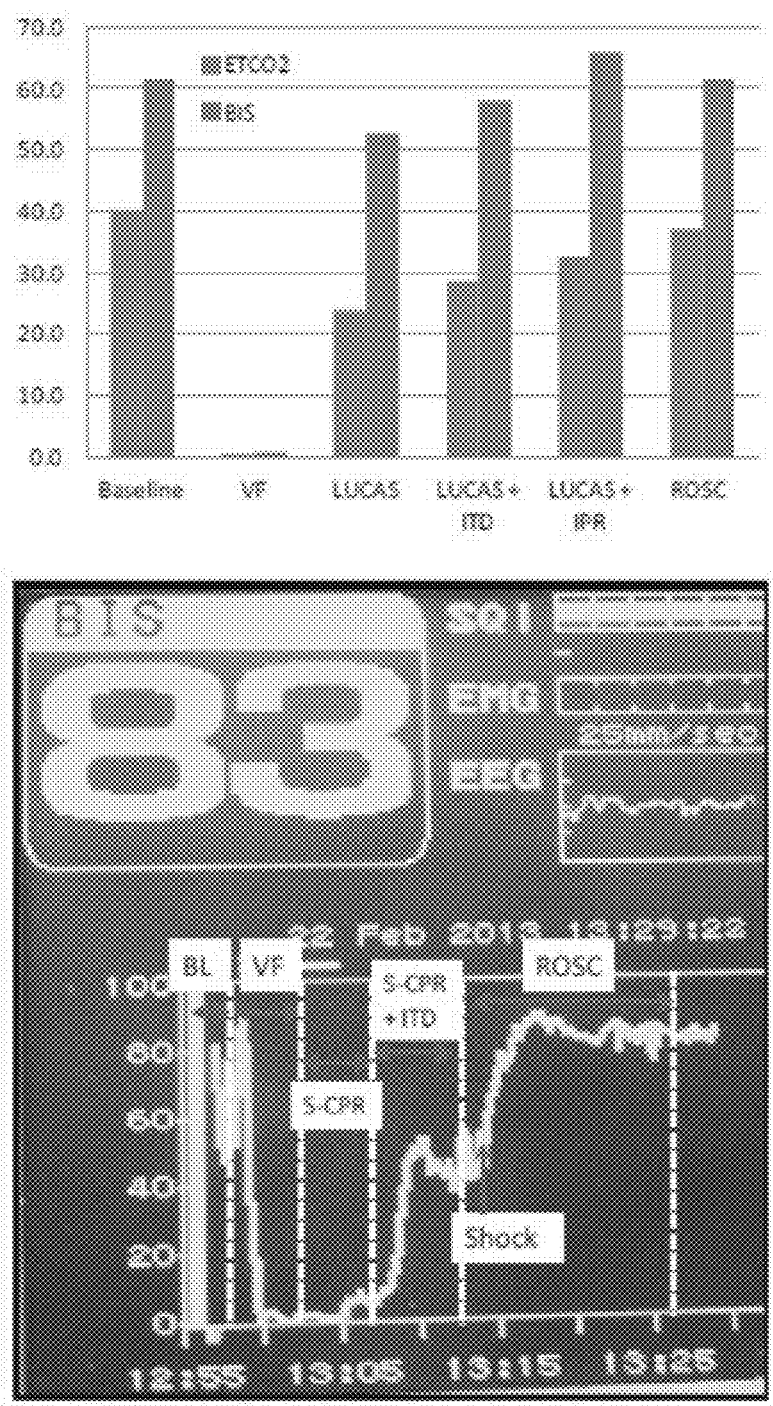
FIG. 1 shows bispectral index (BIS) and end-tidal CO2 (ETCO2) after 6 minutes ventricular fibrillation during differing types of cardiopulmonary resuscitation (CPR), and a BIS screenshot during a typical study.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

Out-of-hospital cardiac arrest (OHCA) is one of the leading causes of death in at least the United States. Even with clinically documented methods of CPR and post-resuscitation care, more than 85-90% of the 350,000 Americans stricken by OHCA die suddenly and unexpectedly annually. Over the past twenty years, Applicants have developed and implemented ways to improve blood flow to the heart and the brain during CPR. With the development of the Applicants' ResQPOD impedance threshold device (ITD) and active compression decompression (ACD) CPR, Applicants have demonstrated that the combination of ITD and ACD CPR (ACD+ITD) can increase survival rates with favorable neurological outcomes by a relative 53% compared with conventional standard CPR (S-CPR). This therapy is based upon the physiological principle that a reduction in intrathoracic pressure during the decompression phase of CPR pulls more venous blood back to the heart, and simultaneously lowers intracranial pressure (ICP) when compared with S-CPR. The reduced ICP lowers cerebral resistance allowing for greater forward flow. Applicants have developed further ways to regulate intrathoracic pressure during CPR based upon this general principle of intrathoracic pressure regulation (IPR) therapy. This approach may significantly increase coronary and cerebral perfusion during CPR and enhance the likelihood for successful resuscitation. Such devices and techniques are described in, for example, U.S. Pat. Nos. 7,082,945, 7,185,649, 7,195,012, 7,195,013, 7,766,011, 7,836,881, and 8,108,204, and U.S. patent application Ser. Nos. 13/175,670, 13/554,458, and 13/852,142, each incorporated herein by reference.

While this progress has saved lives, it has also created exciting new challenges and opportunities. For example, it would be advantageous to provide paramedics with a tool that encourages the continued performance of CPR in instances where the chance of meaningful survival after cardiac arrest is high. It is contemplated herein that new techniques may be needed to determine the likelihood of long-term survivability with favorable neurological function, so that those performing CPR recognize when to continue resuscitation efforts and when to stop. Without such technologies, patients with the potential to be fully resuscitated and restored back to their baseline health may be at high risk of being left for dead due to premature stoppage of CPR, despite actually having a favorable prognosis. The continued performance of CPR may be encouraged by providing rescuers and/or paramedics with indications of brain functioning and/or positive signs of likely long term survival. A new way to assess brain function during CPR may be even more important in years ahead as even more effective ways to successfully resuscitate patients are discovered.

The present disclosure is directed to the non-invasive and rapid determination of the likelihood of neurological viability in patients during CPR. Measuring electroencephalograms (EEGs) during CPR with a non-invasive system that measures the bispectral index may be used together with end tidal (ET) CO2 to determine signs of brain activity that may indicate or be used to predict the chances of recovering from a cardiac arrest with brain function remaining neurologically intact.

EEG measurements may be used intra-operatively to determine the depth of anesthesia and post resuscitation from cardiac arrest as an indicator for brain survival. In some embodiments, EEGs measurements may be used during CPR to help provide a non-invasive window to assess the potential for the individual awakening after OHCA. While this approach may not provide a consistent signal with conventional standard CPR, as brain perfusion is generally less than 20% of normal, it may provide promise during CPR with IPR therapy where brain perfusion can be nearly normal during CPR. Further, when EEG measurements are coupled together with ETCO2—an index of vital organ perfusion—Applicants studies suggest that dual monitoring of these two indicators of brain flow and function may provide a means to predict successful resuscitation with favorable neurological outcome. Thus, the present application is focused on using EEG activity, measured using a bispectral index (BIS) monitor during CPR to predict neurological status during CPR, alone or in combination with another non-invasive measurement, such as ETCO2, as an index to suggest whether rescuers should continue or discontinue CPR. In some embodiments, a data log storage process and data display for EEG and ETCO2 measurements may be employed in an IPR ventilation device for the treatment of patients with OHCA.

Building on animal and human studies that have focused on improving blood flow during CPR, Applicants have shown that a combination of non-invasive technologies that modulate intrathoracic pressures—specifically, ACD+ITD—may be applied in patients with OHCA to improve survival rates with favorable neurological outcomes compared with S-CPR. This combination of devices was found to increase patient survival with favorable neurological function by about 50%, from about 5.9 to 8.8% at hospital discharge (p=0.02), and at one year post cardiac arrest. Further, Applicants have developed strategies to prevent reperfusion injury during CPR using IPR therapy that result in an improvement in neurologically-intact survival after up to 15 minutes of untreated cardiac arrest. Other approaches to reduce the cerebral injury associated with reperfusion after prolonged untreated cardiac arrest may include, for example, using IPR therapy in combination with alternating 20 second pauses followed by 20 seconds of CPR during the first 3 minutes of CPR to provide protection from reperfusion injury. These studies demonstrate that there is a greater potential to fully restore the brain after prolonged untreated cardiac arrest than previously realized, allowing for a prediction of which patients are likely to awake after CPR.

An increased level of consciousness may be achieved during ACD+ITD CPR despite being in a non-perfusing rhythm (cardiac arrest). This type of patient may commonly die because of a highly stenotic or occluded coronary artery where the culprit lesion causes the cardiac arrest and prevents circulation to the myocardium during CPR.

A database containing data from a clinical trial, was examined to determine 1) the frequency of re-arrest; 2) the initial rhythms for subjects that re-arrest; 3) the frequency of gasping during CPR; 4) signs of neurological activity (moving limbs, opening eyes, trying to sit up, late gasping developing after several minutes of CPR) during chest compressions. In an analysis of greater than 2200 subjects who met initial enrollment criteria, the re-arrest rate was about 20% and half of those subjects did not survive to hospital admission. Signs of neurological activity were observed in about 2-12% of subjects depending upon the trial site, and gasping (a favorable prognostic sign suggestive of brain stem perfusion) was observed in about 8.5% of all subjects. About one half of these subjects did not survive to hospital admission as CPR was abandoned. Accordingly, an estimation of about 10-15% of all subjects receiving CPR may actually have the potential to survive and thrive but currently are left to die in the field because there is no way for the rescuer or emergency physician to easily determine whether the afflicted patient has the potential to survive with additional CPR and in-hospital care. In one aspect, the present application may be focused on this patient population. For example, an objective may be at least to develop a non-invasive system to provide the rescuer an indication of whether CPR is warranted beyond the traditional 15-30 minutes based upon the likelihood for neurologically intact survival.

In the course of assessing the effects of IPR therapy using different methods of CPR in animal studies, Applicants discovered that BIS levels vary depending on the type of CPR performed. In an aspect, the term "BIS" is used throughout as a general term for spectral analysis of EEG signals. Also, somatosensory evoked potential monitoring has been employed to assess anesthesia levels and awareness during total intravenous anesthesia (TIVA). Like BIS level, this technique may also prove valuable in assessing brain function and electrical shutdown due to cerebral ischemia. In the Applicants studies, it was observed that even though there was not a significant change in calculated cerebral perfusion pressure, or coronary perfusion pressure, BIS levels increased markedly when IPR therapy was optimized.

During general anesthesia, the BIS may provide a non-invasive measurement of the level of a patient's consciousness. The BIS value may be derived from the patient's EEG tracings, which are a real-time graphical representation of the spontaneously generated electrical potentials in the brain area underlying an electrode. As these EEG patterns diminish with exposure to an anesthetic drug, a BIS monitor may transform the EEG waveform into a dimensionless number ranging from 0 (complete cerebral suppression) to 100 (active cerebral cortex; fully awake and alert). To compute this value, the BIS monitor may process the EEG to detect the presence of cerebral suppression and perform a fast Fourier transform (FFT) on the waveform. The FFT data may be used to compute the ratio of higher frequency waves to lower frequency waves which results in the BIS value. An accompanying variable, the suppression ratio, estimates the percentage of isoelectric (flatline) periods during 63 second epochs. This number may be presented as a value from 0-100%. The suppression ratio may be factored into the overall BIS, and values of 40-60 may represent an appropriate level for general anesthesia.

In an aspect, a concept of using EEG recordings in the form of a BIS index and ETCO2 during CPR as a predictor of outcomes is disclosed. Using conventional CPR, BIS levels remain low and indicative of no significant brain activity, whereas the addition of IPR therapy causes a surprising rise in BIS despite a minimal increase in calculated cerebral perfusion pressure (CerPP). This suggests a non-linear relationship between restoration of consciousness during CPR and the level of cerebral perfusion. The use of CPR that incorporates IPR therapy, as opposed to conventional standard CPR, may cause a sufficient reduction of ICP and an improvement in brain perfusion to allow for restoration of brain electrical activity and, in some cases, near consciousness in the setting of cardiac arrest and CPR. Applicants have previously shown that IPR therapy lowers ICP by actively removing more venous blood from the brain and perhaps by also sequestering more spinal fluid in the intracranial space. The technique may predict the possibility of neurological recovery after OHCA and provide rescuers feedback to encourage additional CPR and/or transport to hospital if the chances of neurologically intact survival are evident. In addition, an EEG activity index level alone or coupled with a non-invasive measure of perfusion such as ETCO2 may be used to titrate the IPR therapy.

Pilot animal work may demonstrate the potential of utilizing EEG measurements and the BIS to demonstrate the potential of this technology to correlate with improved brain perfusion and subsequent neurologically intact survival. In one study to determine the potential synergy between an automated CPR device called the LUCAS and the impedance threshold device (ITD) ResQPOD, after 6 minutes of untreated VF, CPR was performed with the LUCAS device (delivers S-CPR) for 4 minutes and then ITD was added for 4 minutes, and then IPR therapy for 4 minutes. As shown in FIG. 1, BIS levels decreased to zero rapidly after induction of VF, rose to 52 with the S-CPR and then rose again with the addition of the ITD and IPR therapy. ETCO2 levels rose as well in this study from 0 to 33 mmHg. Here, the suppression ratio (SR) or "flatline" periods are typically 0 at baseline, 85 during VF, 4 during S-CPR, and 1 during IPR CPR. These results are consistent with the hypothesis that with enhanced perfusion may result in an increase in electrical activity within the brain, as manifested by the rise in BIS levels. In other studies with 12 minutes of untreated VF and treatment with ACD+ITD alternating with intentional 20 second pauses to reduce reperfusion injury, BIS levels fall to 0 within 2 minutes of VF, and then increase during 4 minutes of CPR back to 60. By contrast, in pigs treated with only SCPR after 12 minutes of VF, the average BIS values at the end of 4 minutes of S-CPR were 10. From survival studies performed before the use of EEGs like BIS to assess brain activity during CPR, treatment strategies designed to reduce reperfusion injury after a prolonged untreated cardiac arrest resulted in a significant number of neurologically intact pigs after 24-48 hours. A BIS level of between 40-60 may indicate a good chance at neurologically intact survival.

Figure 2:
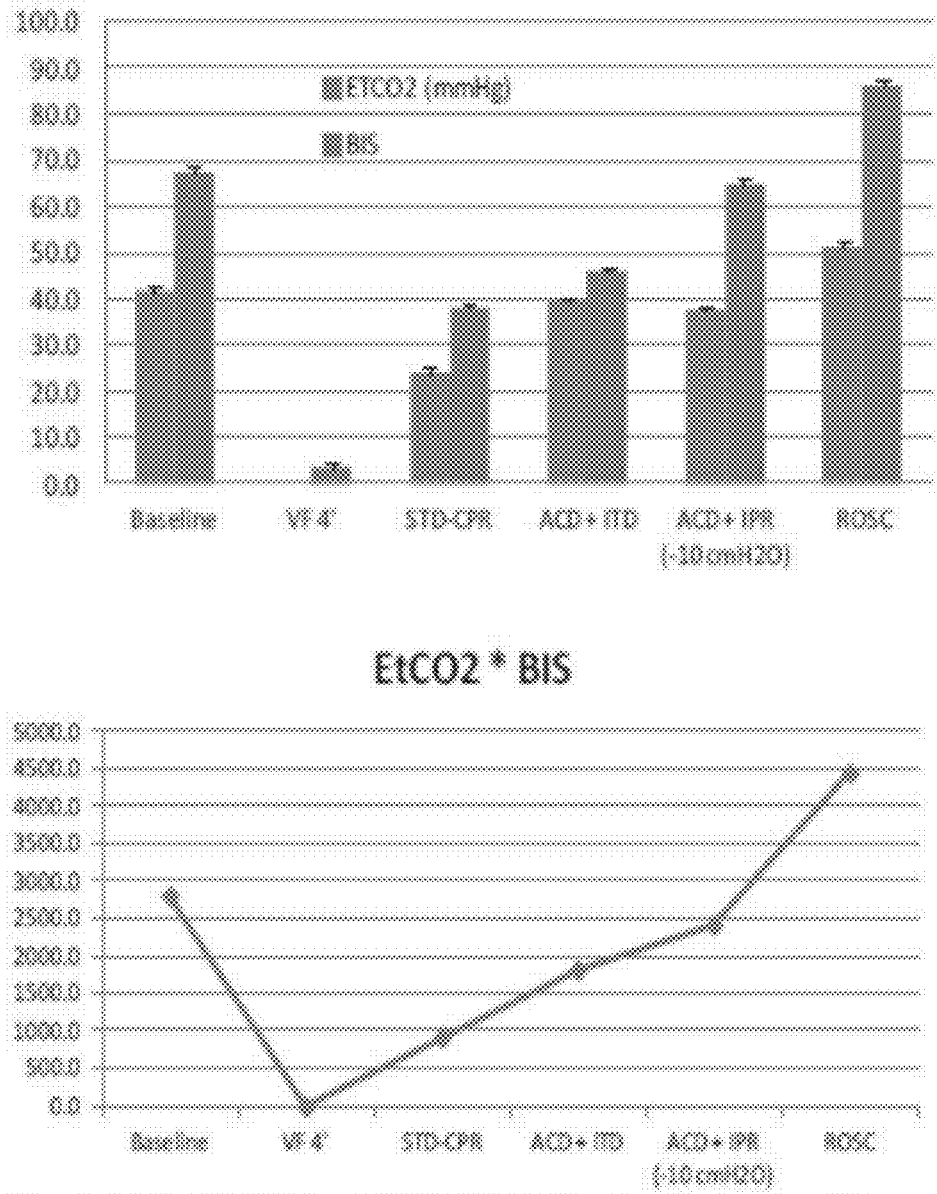
FIG. 2 shows BIS, ETCO2, and BISxETCO2 after 4 minutes VF and multiple methods of CPR.

Applicants have also demonstrated a significant increase in BIS in a pilot study of 6 animals that each had standard CPR (S-CPR), then S-CPR with an ITD (Impedance Threshold Device—that prevents or hinders respiratory gases from reaching the lungs during the relaxation or decompression phase of CPR), followed by ACD-CPR and then ACD-CPR with advanced IPR device (Intrathoracic Pressure Regulation—such as using a vacuum to extract gases from the lungs during the relaxation phase) therapy. These results are shown in FIG. 2 and demonstrate how brain perfusion can be significantly improved with the methods of the present disclosure. In FIG. 2, it is demonstrated how the ETCO2 and BIS product might be utilized to predict not only ROSC but neurologically intact survival. From survival studies with advanced IPR therapy, the neurologically intact survival rate was 100% when ACD+ITD therapy was utilized in a pig model with 8 min of VF in contrast to 10% with S-CPR.

An increase in BIS levels and ETCO2 may be observed during the progression from S-CPR alone to S-CPR+ITD to S-CPR+IPR (advanced ITD therapy which actively creates a vacuum in between positive pressure ventilation that maximizes negative intrathoracic pressures) (FIG. 1) and a similar progression from S-CPR to ACD+ITD to ACD+IPR (FIG. 2). Based on these data, it is contemplated that a study focused specifically on the potential of EEG activity with, for example a BIS value alone or in combination with another non-invasive measurement such as ETCO2, may be evaluated to predict the chances of meaningful survival after cardiac arrest.

In patients undergoing CPR, the non-invasive measurement of cerebral electrical activity, as measured by BIS coupled with the non-invasive measurement of circulation, as measured by ETCO2, may be used to predict the likelihood of neurological recovery and thereby significantly increase survival rates with favorable neurological function after cardiac arrest.

At present, rescuer personnel typically terminate their resuscitation efforts based upon the duration of CPR performed without a guide as to whether or not the patient actually has a chance to survive and thrive. Recent advances in techniques to optimize blood flow to the heart and brain during CPR, reduce reperfusion injury, and improving post-resuscitation restoration of brain function with therapeutic hypothermia, have significantly improved the likelihood for survival with favorable neurological function. These CPR methods are associated with higher BIS and ETCO2 values in the Applicants preliminary studies. Currently it may be difficult to know during CPR which patients may be able to be resuscitated and wake up after successful resuscitation. In one example, perfusion as indicated by ETCO2, for example, and brain wave activity, as measured by BIS for example, may be used to provide a strong physiological signal for the potential to survive and thrive. The predictive ability of each of these physiological indicators may be examined alone, however, new findings support the use of mathematics, such as the mathematical product of these measures, as an indicator for predicting survival with a favorable neurological outcome. Similar to the heart, where both normal electrical and mechanical activity to provide perfusion are needed for life, the brain needs normal electrical activity and perfusion. These physiological cerebral processes may be assessed as a non-invasive means to help determine if successful resuscitation will result in the potential for restoration of full life.

Figure 3:
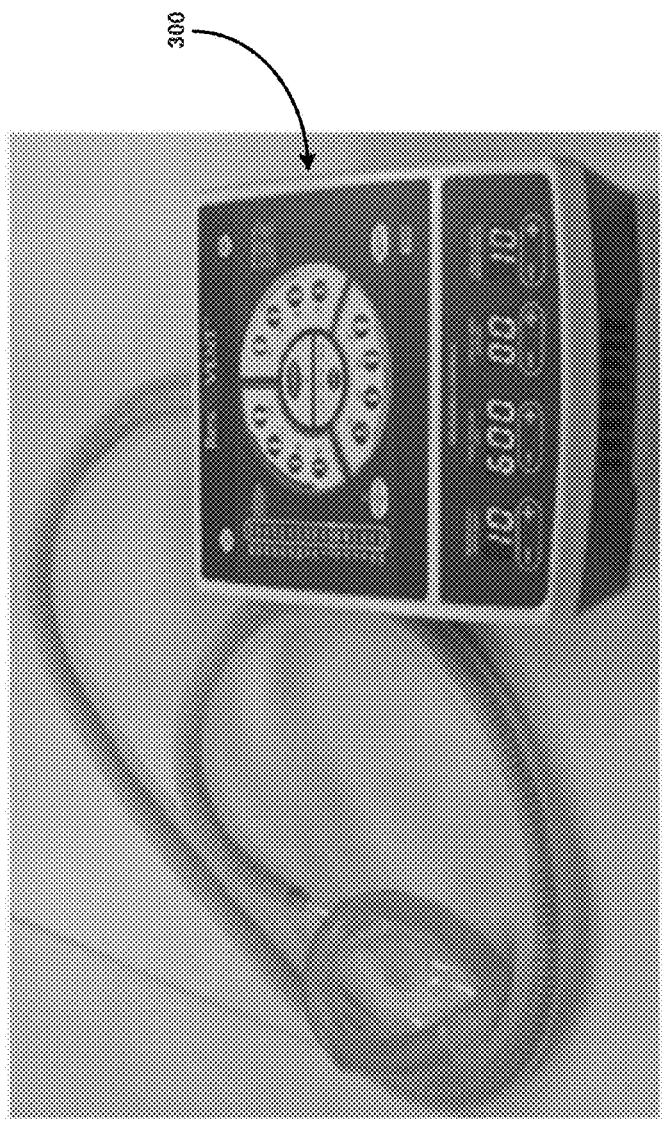
FIG. 3 shows an example vacuum source device that has an impeller to create a vacuum, the example vacuum source device is a transport ventilator with integrated intrathoracic pressure regulation.
Figure 4:
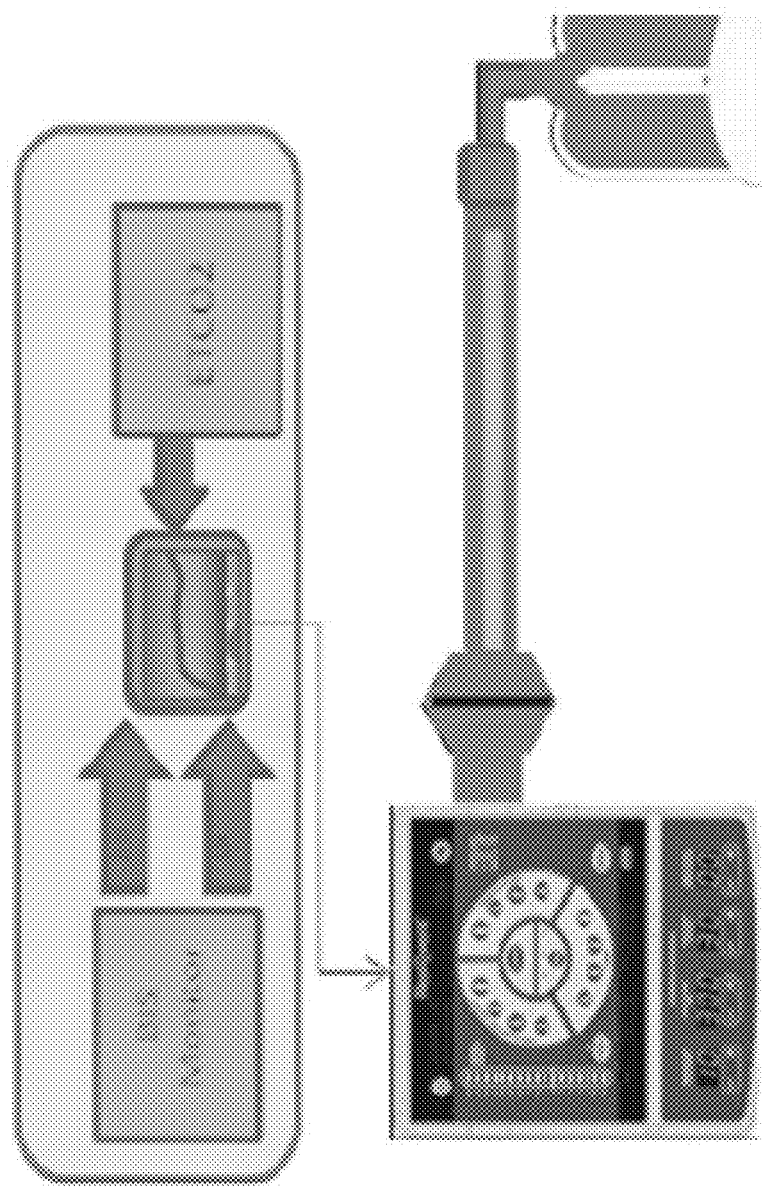
FIG. 4 shows an integrated index calculator and display.

In another aspect, a data log storage process and data display for EEG and ETCO2 measurements may be incorporated in an IPR ventilation device developed for the treatment of patients with OHCA. FIG. 3 shows an exemplary vacuum source device 300 that has an internal impeller configured to push air out of the device 300 through a vent to create an internal vacuum. In general, the device 300 is a transport ventilator with integrated intrathoracic pressure regulation. In one embodiment, the device 300 may correspond to a ResQVENT device, which is a transport ventilator capable of providing IPR therapy as previously described for use during CPR. The device 300 may combine positive pressure ventilation breaths with IPR therapy during the exhalation phase of the breath. The ResQVENT device may be attached to the patient's facemask or endotracheal tube via a coaxial breathing circuit. The ResQVENT's inside tube may convey inspiration gases to the patient and the outside tube may carry gas away from the patient. The apparatus may functionally integrate with existing monitor data streams (e.g., BIS Monitor, Capnometry). In such embodiments, the user interface may receive a Cerebral Resuscitation Assessment indicator which could be described as a brain tissue quality factor. In some embodiments, the monitor may be integrated into the ResQVENT. In other embodiments, the monitor may be a stand-alone monitor that provides data to the ResQVENT as shown in FIG. 4. One non-limiting example of equipment that may function similar to the ResQVENT is described in U.S. Patent Application No. 61/577,565, filed 19 Dec. 2011, the complete disclosure of which is herein incorporated by reference.

With this piece of information (i.e., the Cerebral Resuscitation Assessment indicator), rescuers would be provided with some indication related to the potential viability of the brain, which may provide rescuers guidance or an indication as to whether to continue or discontinue CPR. The device 300, either alone or in combination with other devices, may gather the needed information in one place and mathematically relate the values. To receive this information, inputs from the BIS and/or ETCO2 monitors may require specific software communication methods. In some embodiments, continuous data may be stored in the computer at an acceptable data storage rate to ensure good fidelity.

An electronic interface with the BIS monitor or a comparable EEG system and the ETCO2 monitor may be used to electronically read the BIS and ETCO2 data from the outputs of the two devices. The output data from the devices may then be stored and mathematical calculations performed. The resultant index may be displayed on a user interface/display to provide an easy-to-read index. The user may utilize the index to adjust therapy such as IPR levels, ventilation, compression depth, etc. Software validation methods may be utilized to confirm that the software code is intact and representative of the desired output.

In some embodiments, the ResQVENT may produce a continuously variable IPR level from 0-12 cmH2O. The ResQVENT may be adapted to accept an external digital input, which may control the IPR level based on the inputs from the above described Index calculation. This adaptation may include additional modification of the ResQVENT software to accept an external control signal from the existing serial port. The ResQVENT may be programmed to optimize the beneficial effects of IPR in a particular patient or set of conditions. In some embodiments, the BIS monitor may be available as a module that fits into various multi-parametric bedside monitors. Monitoring packages of BIS and ETCO2 monitors may be physically integrated into a single portable device with its own small graphic display. The single box may quickly connected to a patient experiencing cardiac arrest and be unobtrusive during resuscitation. A quick application of the forehead electrodes and an attachment of the ETCO2 monitor to the airway may enable the user interface to deliver resuscitation feedback to the user.

In some embodiments, the device 300 may be configured for predicting the likelihood of survival of a particular individual with favorable neurological function during a cardiopulmonary resuscitation (CPR) procedure. As described herein, the device 300 may include a circulation enhancement device (e.g., a vacuum source, a pressure responsive valve, and the like) that is configured to enhance a person's circulation while performing CPR on the person. The device 300 may also include an EEG sensor and/or a bispectral index monitor that is configured to measure an EEG signal of the person. The device 300 may further include a non-invasive sensor and/or a capnography monitor to measure circulation data on the person's circulation.

In some embodiments, the device 300 may include a computing device having a processor that is configured to receive and process the EEG signal and the circulation data and to produce a prediction of the likelihood of survival of the person with favorable neurological function. In some embodiments, the device 300 may include a vacuum source that is configured to extract respiratory gases from the airway of the person to create an intrathoracic vacuum to lower pressures in the thorax. The vacuum source may include an impeller that creates the vacuum. The pressures may be lowered in the thorax in order to achieve: enhanced flow of blood to the heart of the particular individual, lower pressures in the thorax in order to lower intracranial pressures of the person, and/or lower pressures in the thorax in order to enhance cerebral profusion pressures of the person. In some embodiments, the device 300 may include a pressure responsive valve that is configured to prevent respiratory gases from entering the lungs during at least a portion of a relaxation or decompression phase of CPR to create an intrathoracic vacuum that lowers pressure in the thorax in order to achieve: enhanced flow of blood to the heart of the particular individual, lowered intracranial pressures of the particular individual, and/or enhanced cerebral profusion pressures of the particular individual.

Figure 5:
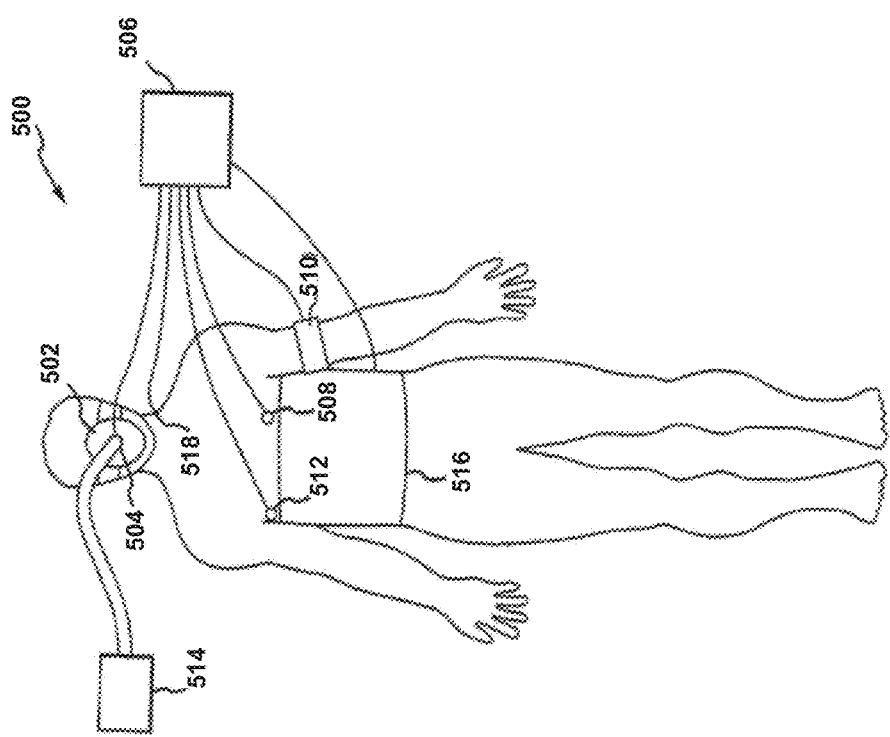
FIG. 5 shows an example treatment system in accordance with the present disclosure.

FIG. 5 shows an example treatment system 500 in accordance with the present disclosure. The system 500 may include a facial mask 502 and a valve system 504. The valve system 504 may be coupled to a controller 506. In turn, the controller 506 may be used to control an impedance level of the valve system 504. The level of impedance may be varied based on measurements of physiological parameters, or using a programmed schedule of changes. The system 500 may include a wide variety of sensors and/or measuring devices to measure any of a number physiological parameters. Such sensors or measuring devices may be integrated within or coupled to the valve system 504, the facial mask 502, etc., or may be separate depending on implementation. An example of sensors and/or measuring devices may include a pressure transducer for taking pressure measurements (such as intrathoracic pressures, intracranial pressures, intraocular pressures), a flow rate measuring device for measuring the flow rate of air into or out of the lungs, or a CO2 sensor for measuring expired CO2. Examples of other sensors or measuring devices include a heart rate sensor 508, a blood pressure sensor 510, and/or a temperature sensor 512. These sensors may also be coupled to the controller 506 so that measurements may be recorded. Further, it will be appreciated that other types of sensors and/or measuring devices may be coupled to the controller 506 and may be used to measure various physiological parameters, such as bispectral index, oxygen saturation and/or blood levels of O2, blood lactate, blood pH, tissue lactate, tissue pH, blood pressure, pressures within the heart, intrathoracic pressures, positive end expiratory pressure, respiratory rate, intracranial pressures, intraocular pressures, respiratory flow, oxygen delivery, temperature, end tidal CO2, tissue CO2, cardiac output, and many others.

In some cases, the controller 506 may be used to control the valve system 504, to control any sensors or measuring devices, to record measurements, and/or to perform any comparisons. Alternatively, a set of computers and/or controllers may be used in combination to perform such tasks. This equipment may have appropriate processors, display screens, input and output devices, entry devices, memory or databases, software, and the like needed to operate the system 500. A variety of devices may also be coupled to controller to cause the person to artificially inspire. For example, such devices may comprise a ventilator 514, an iron lung cuirass device 516 or a phrenic nerve stimulator 518. The ventilator 514 may be configured to create a negative intrathoracic pressure within the person, or may be a high frequency ventilator capable of generating oscillations at about 200 to about 2000 per minute. Other embodiments are possible. For example, in some embodiments, the device 300 of FIG. 3 and/or FIG. 4 may substitute for the ventilator 514.

In some embodiments, the system 500 may be configured for predicting the likelihood of survival of a particular individual with favorable neurological function during a cardiopulmonary resuscitation (CPR) procedure. To predict the likelihood of survival, the system 500 may include a module that is configured to calculate a bispectral index value of the particular individual during the CPR procedure. The module may be a bispectral index monitor that is configured to calculate the bispectral index value. The system 500 may also include a module that is configured to calculate a non-invasive measure of circulation of the particular individual during the CPR procedure. The module may be a capnography monitor that calculates the non-invasive measure of circulation. The system 500 may further include a module, such as a computing device processor, that is configured to output a prediction for the likelihood of survival based on the bispectral index value and the non-invasive measure of circulation.

In some embodiments, the system 500 may additionally include a module that is configured to obtain an electroencephalogram (EEG) signal of the particular individual during the CPR procedure. It is contemplated that any device or system that is configured to obtain an EEG signal may be used to acquire the same. For example, a dedicated EEG sensor may be used to obtain an EEG signal during the CPR procedure.

In some embodiments, the non-invasive measure of circulation may include a measure of concentration or partial pressure of carbon dioxide in respiratory gases of the particular individual. In some embodiments, the system 500 may additionally include a module, such as a computing device processor, that is configured to determine whether sedation is needed during and/or following the CPR procedure based on the bispectral index value and the non-invasive measure of circulation.

Figure 6:
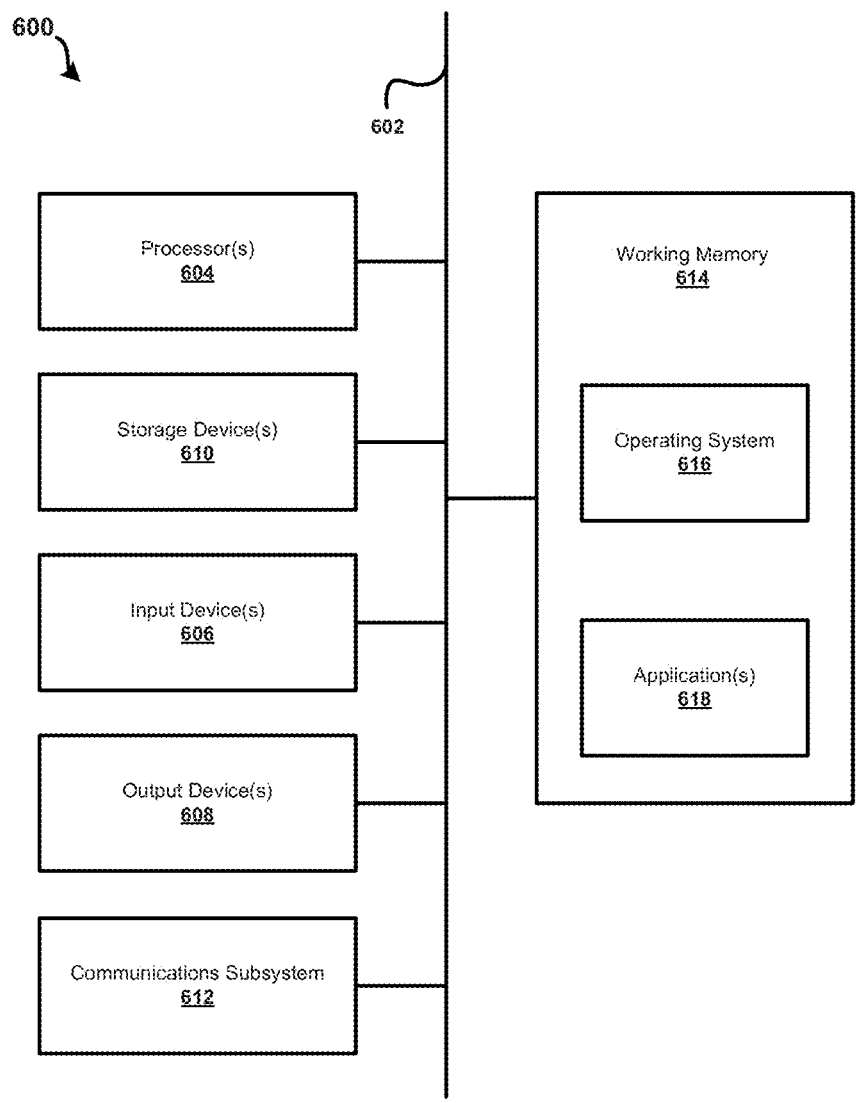
FIG. 6 shows an example computing system or device.

FIG. 6 shows an example computer system or device 600 in accordance with the present disclosure. An example of a computer system or device includes a medical device, a desktop computer, a laptop computer, a tablet computer, a personal data assistant, smartphone, and/or any other type of machine configured for performing calculations.

The computer system 600 may be wholly or at least partially incorporated as part of previously-described computing devices, such as the devices described above in connection with one or more of FIGS. 1-5. The example computer device 600 may be configured to perform and/or include instructions that, when executed, cause the computer system 600 to perform a method for predicting the likelihood of survival of a particular individual with favorable neurological function. The example computer device 600 may be configured to perform and/or include instructions that, when executed, cause the computer system 600 to implement or be incorporated within a computing system or apparatus configured for predicting the likelihood of survival of a particular individual with favorable neurological function. The example computer device 600 may be configured to perform and/or include instructions that, when executed, cause the computer system 600 to perform a method for determining whether sedation is needed while performing cardiopulmonary resuscitation. The example computer device 600 may be configured to perform and/or include instructions that, when executed, cause the computer system 600 to perform a method for determining whether sedation is needed after concluding cardiopulmonary resuscitation.

The computer device 600 is shown comprising hardware elements that may be electrically coupled via a bus 602 (or may otherwise be in communication, as appropriate). The hardware elements may include a processing unit with one or more processors 604, including without limitation one or more general-purpose processors and/or one or more special-purpose processors (such as digital signal processing chips, graphics acceleration processors, and/or the like); one or more input devices 606, which may include without limitation a remote control, a mouse, a keyboard, and/or the like; and one or more output devices 608, which may include without limitation a presentation device (e.g., television), a printer, and/or the like.

The computer system 600 may further include (and/or be in communication with) one or more non-transitory storage devices 610, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer device 600 might also include a communications subsystem 612, which may include without limitation a modem, a network card (wireless or wired), an infrared communication device, a wireless communication device, and/or a chipset (such as a Bluetooth™ device, an 602.11 device, a WiFi device, a WiMax device, cellular communication facilities (e.g., GSM, WCDMA, LTE, etc.), and/or the like. The communications subsystem 612 may permit data to be exchanged with a network (such as the network described below, to name one example), other computer systems, and/or any other devices described herein. In many embodiments, the computer system 600 may further comprise a working memory 614, which may include a random access memory and/or a read-only memory device, as described above.

The computer device 600 also may comprise software elements, shown as being currently located within the working memory 614, including an operating system 616, device drivers, executable libraries, and/or other code, such as one or more application programs 618, which may comprise computer programs provided by various embodiments, and/or may be designed to implement methods, and/or configure systems, provided by other embodiments, as described herein. By way of example, one or more procedures described with respect to the method(s) discussed above, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code might be stored on a non-transitory computer-readable storage medium, such as the storage device(s) 610 described above. In some cases, the storage medium might be incorporated within a computer system, such as computer system 600. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer device 600 and/or might take the form of source and/or installable code, which, upon compilation and/or installation on the computer system 600 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer device 600) to perform methods in accordance with various embodiments of the invention. According to a set of embodiments, some or all of the procedures of such methods are performed by the computer system 600 in response to processor 604 executing one or more sequences of one or more instructions (which might be incorporated into the operating system 616 and/or other code, such as an application program 618) contained in the working memory 614. Such instructions may be read into the working memory 614 from another computer-readable medium, such as one or more of the storage device(s) 610. Merely by way of example, execution of the sequences of instructions contained in the working memory 614 may cause the processor(s) 604 to perform one or more procedures of the methods described herein.

The terms "machine-readable medium" and "computer-readable medium," as used herein, may refer to any medium that participates in providing data that causes a machine to operate in a specific fashion. In an embodiment implemented using the computer device 600, various computer-readable media might be involved in providing instructions/code to processor(s) 604 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 610. Volatile media may include, without limitation, dynamic memory, such as the working memory 614.

Example forms of physical and/or tangible computer-readable media may include a floppy disk, a flexible disk, hard disk, magnetic tape, or any other magnetic medium, a CD-ROM, any other optical medium, a RAM, a PROM, EPROM, a FLASH-EPROM, any other memory chip or cartridge, or any other medium from which a computer may read instructions and/or code.

Various forms of computer-readable media may be involved in carrying one or more sequences of one or more instructions to the processor(s) 604 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 600.

The communications subsystem 612 (and/or components thereof) generally will receive signals, and the bus 602 then might carry the signals (and/or the data, instructions, etc. carried by the signals) to the working memory 614, from which the processor(s) 604 retrieves and executes the instructions. The instructions received by the working memory 614 may optionally be stored on a non-transitory storage device 610 either before or after execution by the processor(s) 604.

Figure 7:
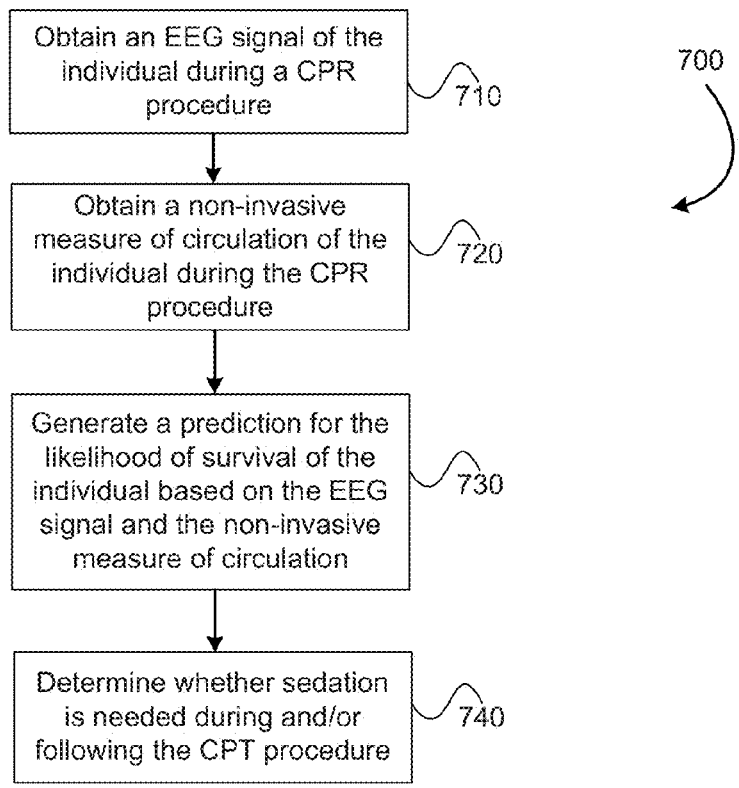
FIG. 7 shows a method for predicting the likelihood of survival of a particular individual with favorable neurological function during a cardiopulmonary resuscitation (CPR) procedure.

FIG. 7 shows a method for predicting the likelihood of survival of a particular individual with favorable neurological function during a cardiopulmonary resuscitation (CPR) procedure. At block 710, an electroencephalogram (EEG) signal of the particular individual is obtained during the CPR procedure. At block 720, a non-invasive measure of circulation of the particular individual is obtained during the CPR procedure. At block 730, a prediction for the likelihood of survival of the particular individual with favorable neurological function is generated based on the EEG signal and the non-invasive measure of circulation.

In some embodiments, the method includes performing an intrathoracic pressure regulation procedure and/or a reperfusion injury protection procedure during the CPR procedure. It is contemplated that any of a number of such procedures may be performed during the CPR procedure such as, for example, performing a stutter CPR procedure, administering anesthetics at or during the CPR procedure, administering sodium nitroprusside in connection with the CPR procedure, and the like. Exemplary procedures and techniques are described in U.S. patent application Ser. Nos. 12/819,959, 13/026,459, 13/175,670, 13/554,986, 61/509,994, and 61/577,565, each of which are incorporated herein by reference.

In some embodiments, the prediction for the likelihood of survival of the particular individual with favorable neurological function may be generated based on a mathematical product of the EEG signal and the non-invasive measure of circulation. In some embodiments, the method may also include measuring the EEG signal using a bispectral index monitor. In some embodiments, the non-invasive measure of circulation of the particular individual may be obtained by monitoring the concentration or partial pressure of carbon dioxide in the respiratory gases of the particular individual. In other embodiments, however, other means may be used to obtain the non-invasive measure of circulation, such as diffuse correlation spectroscopy or impedance changes measured across the thorax or other body parts.

At block 740, the method may optionally include determining whether sedation is needed during and/or following the CPR procedure based on the EEG signal and the non-invasive measure of circulation. Here, when the EEG signal and/or a product of the EEG signal and a measure of circulation (e.g., end tidal CO2) reaches a threshold value during CPR, a care provider may recognize that it may be appropriate to deliver a low dose of a sedative (e.g., medazelam and the like) to prevent the patient from undergoing cardiac arrest or from becoming too agitated.

In some embodiments, the method may further include extracting respiratory gases from the airway of the particular individual to create an intrathoracic vacuum that lowers pressure in the thorax in order to achieve: enhancing the flow of blood to the heart of the particular individual, lowering intracranial pressures of the particular individual, and/or enhancing cerebral profusion pressures of the particular individual. Any device and/or system that is configured to create a vacuum and that may be coupled to an individual so as to create an intrathoracic vacuum may be used to lower pressure in the thorax and/or to artificially inspire, such as a ventilator, iron lung cuirass device, a phrenic nerve stimulator, and the like. In some embodiments, the method may additionally include at least periodically delivering a positive pressure breath to the particular individual to provide ventilation.

In some embodiments, the method may additionally include preventing air from at least temporarily entering the particular individual's lungs during at least a portion of a relaxation or decompression phase of the CPR procedure to create an intrathoracic vacuum that lowers pressure in the thorax in order to: enhance the flow of blood to the heart of the particular individual, lower the intracranial pressures of the particular individual, and/or enhance cerebral profusion pressures of the particular individual.

Figure 8:
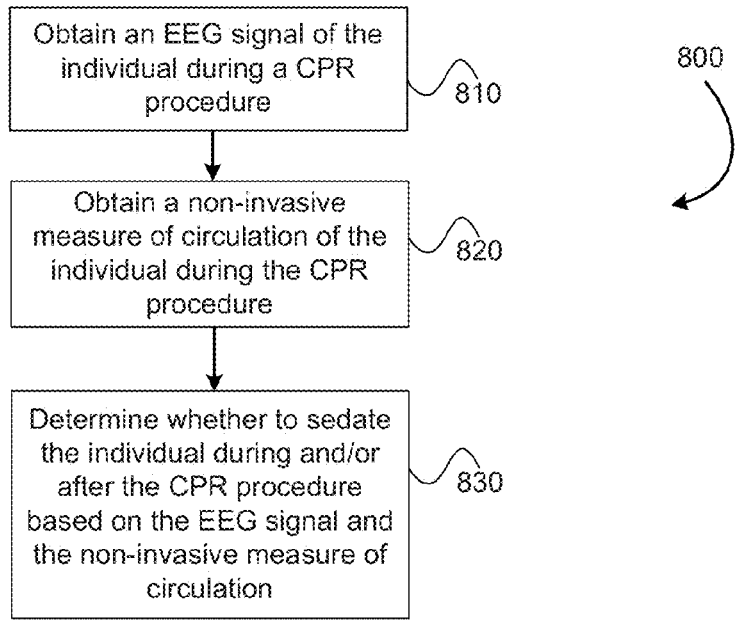
FIG. 8 shows a method for determining whether sedation is needed while performing cardiopulmonary resuscitation (CPR) on a particular individual.

FIG. 8 shows a method for determining whether sedation is needed while performing cardiopulmonary resuscitation (CPR) on a particular individual. At block 810, an electroencephalogram (EEG) signal of the particular individual is obtained during a CPR procedure. At block 820, a non-invasive measure of circulation of the particular individual is obtained during the CPR procedure. At block 830, it is determined whether to sedate the individual while and/or after performing CPR based upon the product of the EEG signal and a non-invasive measure of circulation.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the example embodiments described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for predicting the likelihood of survival of a particular individual with intact neurological function during a cardiopulmonary resuscitation (CPR) procedure, comprising:
   obtaining, with an electroencephalogram (EEG) sensor, an EEG signal of the particular individual during the CPR procedure;
   obtaining, with a non-invasive sensor, a non-invasive measure of circulation of the particular individual during the CPR procedure; and
   generating, with a processor, a prediction for the likelihood of survival of the particular individual with intact neurological function, based on a mathematical operation based on the EEG signal and the non-invasive measure of circulation.

2. The method of claim 1, wherein the CPR procedure comprises an intrathoracic pressure regulation procedure or a reperfusion injury protection procedure.

3. The method of claim 2, wherein the CPR procedure further comprises a stutter CPR procedure.

4. The method of claim 2, wherein the CPR procedure further comprises administration of an anesthetic.

5. The method of claim 2, wherein the CPR procedure further comprises administration of sodium nitroprusside.

6. The method of claim 1, wherein obtaining the EEG signal comprises measuring the EEG signal using a bispectral index monitor.

7. The method of claim 1, wherein obtaining the non-invasive measure of circulation of the particular individual comprises monitoring the concentration or partial pressure of carbon dioxide in respiratory gases of the particular individual.

8. The method of claim 1, further comprising determining whether sedation is needed during the CPR procedure based on the EEG signal and the non-invasive measure of circulation.

9. The method of claim 1, further comprising determining whether sedation is needed following resuscitation of the particular individual based on the EEG signal and the non-invasive measure of circulation.

10. The method of claim 1, further comprising extracting respiratory gases from the airway of the particular individual to create an intrathoracic vacuum that lowers pressure in the thorax in order to achieve at least one of:
   enhancing the flow of blood to the heart of the particular individual;
   lowering intracranial pressures of the particular individual; or
   enhancing cerebral profusion pressures of the particular individual.

11. The method of claim 10, further comprising at least periodically delivering a positive pressure breath to the particular individual to provide ventilation.

12. The method of claim 1, further comprising preventing air from at least temporarily entering the particular individual's lungs during at least a portion of a relaxation or decompression phase of the CPR procedure to create an intrathoracic vacuum that lowers pressure in the thorax in order to achieve at least one of:
   enhanced flow of blood to the heart of the particular individual;
   lowered intracranial pressures of the particular individual; or
   enhanced cerebral profusion pressures of the particular individual.

13. The method of claim 12, further comprising at least periodically delivering a positive pressure breath to the particular individual to provide ventilation.

14. A computing system configured for predicting the likelihood of survival of a particular individual with intact neurological function during a cardiopulmonary resuscitation (CPR) procedure, comprising:
   a module configured to obtain an electroencephalogram (EEG) signal of the particular individual during the CPR procedure;
   a module configured to obtain a non-invasive measure of circulation of the particular individual during the CPR procedure; and
   a module configured to output a prediction for the likelihood of survival of the particular individual with intact neurological function based on a mathematical operation based on the EEG signal and the non-invasive measure of circulation.

15. The system of claim 14, further comprising a bispectral index monitor that is configured to calculate a bispectral index value of the particular individual based on the EEG signal.

16. The system of claim 14, wherein the module configured to obtain the non-invasive measure of circulation comprises a capnography monitor that is configured to calculate the non-invasive measure of circulation of the particular individual.

17. The system of claim 14, wherein the module configured to output the prediction for the likelihood of survival comprises a computing device processor, and wherein the prediction is based on a bispectral index value and the non-invasive measure of circulation.

18. The system of claim 14, wherein the module configured to obtain the EEG signal comprises an EEG sensor.

19. The system of claim 14, wherein the non-invasive measure of circulation of the particular individual is a measure of concentration or partial pressure of carbon dioxide in respiratory gases of the particular individual.

20. The system of claim 14, further comprising a module configured to determine whether sedation is needed during the CPR procedure based on the non-invasive measure of circulation and a bispectral index value calculated from the EEG signal.

21. The system of claim 20, wherein the module configured to determine whether sedation is needed comprises a computing device processor.

22. The system of claim 14, further comprising a module configured to determine whether sedation is needed following resuscitation of the particular individual based on the non-invasive measure of circulation and a bispectral index value calculated from the EEG signal.

23. The system of claim 22, wherein the module configured to determine whether sedation is needed following resuscitation of the particular individual comprises a computing device processor.

24. An apparatus configured for predicting the likelihood of survival of a particular individual with intact neurological function during a cardiopulmonary resuscitation (CPR) procedure, comprising:
- a circulation enhancement device that is configured to enhance the particular individual's circulation during the CPR procedure;
- an electroencephalogram (EEG) sensor that is configured to measure an EEG signal of the particular individual;
- a non-invasive sensor that is configured to measure circulation data of the particular individual; and
- a computing device having a processor that is configured to receive and process the EEG signal and the circulation data, and to produce a prediction of the likelihood of survival of the particular individual with intact neurological function based on a mathematical product of the EEG signal and the circulation data.

25. The apparatus of claim 24, wherein the EEG sensor comprises a bispectral index monitor for measuring the EEG signal, and wherein the non-invasive sensor comprises a capnography monitor.

26. The apparatus of claim 24, wherein the circulation enhancement device includes either or both a vacuum source or a pressure responsive valve.

27. The apparatus of claim 24, further comprising a vacuum source configured to extract respiratory gases from the airway of the particular individual to create an intrathoracic vacuum to lower pressures in the thorax, wherein the vacuum source comprises an impeller that creates the vacuum, and wherein the pressures are lowered in the thorax in order to achieve at least one of:
- enhanced flow of blood to the heart of the particular individual;
- lower pressures in the thorax in order to lower intracranial pressures of the particular individual; and
- lower pressures in the thorax in order to enhance cerebral profusion pressures of the particular individual.

28. The apparatus of claim 24, further comprising a pressure responsive valve configured to prevent respiratory gases from entering the lungs during at least a portion of a relaxation or decompression phase of CPR to create an intrathoracic vacuum that lowers pressure in the thorax in order to achieve at least one of:
- enhanced flow of blood to the heart of the particular individual;
- lowered intracranial pressures of the particular individual; and
- enhanced cerebral profusion pressures of the particular individual.

29. A method for determining whether sedation is needed while performing cardiopulmonary resuscitation (CPR) on a particular individual, comprising:
- obtaining an electroencephalogram (EEG) signal of the particular individual during a CPR procedure;
- obtaining a non-invasive measure of circulation of the particular individual during the CPR procedure; and
- determining whether to sedate the individual while performing CPR based upon a mathematical operation based on the EEG signal and the non-invasive measure of circulation.

30. A method for determining whether sedation is needed after concluding cardiopulmonary resuscitation (CPR) on a particular individual, comprising:
- obtaining an electroencephalogram (EEG) signal of the particular individual during a CPR procedure;
- obtaining a non-invasive measure of circulation of the particular individual during the CPR procedure; and
- determining whether to sedate the individual after performing CPR based upon a mathematical operation based on the EEG signal and the non-invasive measure of circulation.

31. A device configured to predict the likelihood of survival of a particular individual with intact neurological function during a cardiopulmonary resuscitation (CPR) procedure, comprising:
- an electroencephalogram (EEG) sensor that is configured to measure an EEG signal of the particular individual during the CPR procedure; and
- a non-invasive sensor that is configured to measure circulation data of the particular individual during the CPR procedure; and
- a processor configured or programmed to receive and process the EEG signal and the circulation data to generate a prediction for the likelihood of survival of the particular individual with intact neurological function based on a mathematical operation based on the EEG signal and the circulation data.

32. The device of claim 31, wherein the EEG sensor comprises a bispectral index monitor for measuring the EEG signal, and wherein the non-invasive sensor comprises a capnography monitor.

33. The device of claim 31, further comprising a vacuum source configured to extract respiratory gases from the airway of the particular individual to create an intrathoracic vacuum to lower pressures in the thorax, wherein the vacuum source comprises an impeller that creates the vacuum, and wherein the pressures are lowered in the thorax in order to achieve at least one of:
- enhanced flow of blood to the heart of the particular individual;
- lower pressures in the thorax in order to lower intracranial pressures of the particular individual; and
- lower pressures in the thorax in order to enhance cerebral profusion pressures of the particular individual.

34. The device of claim 31, further comprising a pressure responsive valve configured to prevent respiratory gases from entering the lungs during at least a portion of a relaxation or decompression phase of CPR to create an intrathoracic vacuum that lowers pressure in the thorax in order to achieve at least one of:
- enhanced flow of blood to the heart of the particular individual;
- lowered intracranial pressures of the particular individual; and
- enhanced cerebral profusion pressures of the particular individual.

* * * * *